US010289802B2

(12) United States Patent
Qiu et al.

(10) Patent No.: US 10,289,802 B2
(45) Date of Patent: May 14, 2019

(54) SPANNING-TREE PROGRESSION ANALYSIS OF DENSITY-NORMALIZED EVENTS (SPADE)

(75) Inventors: Peng Qiu, Houston, TX (US); Andrew J. Gentles, San Jose, CA (US); Sylvia K. Plevritis, Palo Alto, CA (US); Garry Nolan, Palo Alto, CA (US); Karen Sachs, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 464 days.

(21) Appl. No.: 13/411,492

(22) Filed: Mar. 2, 2012

(65) Prior Publication Data

US 2013/0060775 A1 Mar. 7, 2013

Related U.S. Application Data

(63) Continuation-in-part of application No. 13/338,237, filed on Dec. 27, 2011, now abandoned.

(60) Provisional application No. 61/427,467, filed on Dec. 27, 2010, provisional application No. 61/449,557, filed on Mar. 4, 2011.

(51) Int. Cl.
| *G06F 19/00* | (2018.01) |
| *G06F 19/20* | (2011.01) |
| *G06F 19/24* | (2011.01) |
| *G06F 19/26* | (2011.01) |

(52) U.S. Cl.
CPC .............. *G06F 19/24* (2013.01); *G06F 19/20* (2013.01); *G06F 19/26* (2013.01)

(58) Field of Classification Search
None
See application file for complete search history.

(56) References Cited

U.S. PATENT DOCUMENTS

| 4,839,853 A | 6/1989 | Deerwester et al. |
| 5,040,133 A | 8/1991 | Feintuch et al. |
| 5,179,643 A | 1/1993 | Homma et al. |
| 5,263,120 A | 11/1993 | Bickel |
| 5,359,724 A | 10/1994 | Earle |
| 5,555,196 A | 9/1996 | Asano et al. |
| 5,647,058 A | 7/1997 | Agrawal et al. |
| 5,675,819 A | 10/1997 | Schuetze |
| 5,703,959 A | 12/1997 | Asano et al. |
| 5,710,460 A | 1/1998 | Leidy et al. |
| 5,745,749 A | 4/1998 | Onodera |
| 5,787,422 A | 7/1998 | Tukey et al. |
| 5,819,258 A | 10/1998 | Vaithyanathan et al. |
| 5,822,218 A | 10/1998 | Moosa et al. |
| 5,832,182 A | 11/1998 | Zhang et al. |
| 5,857,179 A | 1/1999 | Vaithyanathan et al. |
| 5,864,845 A | 1/1999 | Voorhees et al. |
| 5,940,832 A | 8/1999 | Hamada et al. |
| 5,971,596 A | 10/1999 | Nishikawa et al. |
| 6,003,029 A | 12/1999 | Agrawal et al. |
| 6,038,557 A | 3/2000 | Silverstein |
| 6,049,797 A | 4/2000 | Guha et al. |
| 6,092,072 A | 7/2000 | Guha et al. |
| 6,134,541 A | 10/2000 | Castelli et al. |
| 6,195,659 B1 | 2/2001 | Hyatt et al. |
| 6,269,376 B1 | 7/2001 | Dhillon et al. |
| 6,353,832 B1 | 3/2002 | Acharya et al. |
| 6,381,605 B1 | 4/2002 | Kothuri et al. |
| 6,397,166 B1 | 5/2002 | Leung et al. |
| 6,466,946 B1 | 10/2002 | Mishra et al. |
| 6,487,546 B1 | 11/2002 | Witkowski et al. |
| 6,505,205 B1 | 1/2003 | Kothuri et al. |
| 6,584,456 B1 | 6/2003 | Dom et al. |
| 6,640,227 B1 | 10/2003 | Andreev et al. |
| 6,643,629 B2 | 11/2003 | Ramaswamy et al. |
| 6,684,177 B2 | 1/2004 | Mishra et al. |
| 6,728,715 B1 | 4/2004 | Astley et al. |
| 6,751,621 B1 | 6/2004 | Calistri-Yeh et al. |
| 6,829,561 B2 | 12/2004 | Keller et al. |
| 7,035,775 B2 | 4/2006 | Abe et al. |
| 7,472,062 B2 | 12/2008 | Chaudhari et al. |
| 7,523,117 B2 | 4/2009 | Zhang et al. |
| 7,587,280 B2 | 9/2009 | Alessi et al. |
| 7,653,509 B2 | 1/2010 | Bagwell et al. |
| 7,853,432 B2 | 12/2010 | Carter et al. |
| 2002/0091667 A1 | 7/2002 | Jaipuria et al. |
| 2003/0224344 A1 | 12/2003 | Shamir et al. |
| 2004/0059521 A1 | 3/2004 | Han et al. |
| 2004/0267686 A1 | 12/2004 | Chayes et al. |
| 2005/0111386 A1 | 5/2005 | Jain et al. |
| 2007/0100880 A1 | 5/2007 | Buscema et al. |
| 2012/0191357 A1 | 7/2012 | Qiu et al. |

FOREIGN PATENT DOCUMENTS

| KR | 1020060086531 A | 8/2006 |
| WO | 2002093810 A2 | 11/2002 |

OTHER PUBLICATIONS

Zare et al. (BMC Bioinformatics (2010) vol. 11:403 (1-16).*
Flowjo, Basic Tutorial, Data Analysis Software for Flow Cytometry, FlowJo, LLC, Version 2.0, Revised Jan. 1, 2018, 45 pgs.
Aiba et al., "Defining Developmental Potency and Cell Lineage Trajectories by Expression Profiling of Differentiating Mouse Embryonic Stem Cells", DNA Research, Jan. 2009, vol. 16, pp. 73-80; published online Dec. 26, 2008.
Ashwell et al., "The Many Paths to p38 Mitogen-Activated Protein Kinase Activation in the Immune System", Nature Reviews Immunology, 6:532-540, 2006.
Bandura et al., "Mass Cytometry: Technique for Real Time Single Cell Multitarget Immunoassay Based on Inductively Coupled Plasma Time-of-Flight Mass Spectrometry", Analytical Chemistry, 81(16):6813-6822, 2009.
Bendall et al., "Single-Cell Mass Cytometry of Differential Immune and Drug Responses Across a Human Hematopoietic Continuum", Science, May 6, 2011, vol. 332, No. 6030, pp. 687-696.

(Continued)

*Primary Examiner* — Lori A. Clow
(74) *Attorney, Agent, or Firm* — KPPB LLP

(57) ABSTRACT

Methods and systems for determining progression and other characteristics of microarray expression levels and similar information, alternatively using a network or communications medium or tangible storage medium or logic processor.

15 Claims, 13 Drawing Sheets
(11 of 13 Drawing Sheet(s) Filed in Color)

(56) References Cited

OTHER PUBLICATIONS

Boedigheimer et al., "Mixture Modeling Approach to Flow Cytometry Data", Cytometry A., May 2008, Published online Mar. 27, 2008, vol. 73, No. 5, pp. 421-429.
Bryder et al., "Hematopoietic Stem Cells: The Paradigmatic Tissue-Specific Stem Cell", American Journal of Pathology, Aug. 2006, vol. 169, No. 2, pp. 338-346.
Chan et al., "Statistical Mixture Modeling for Cell Subtype Identification in Flow Cytometry", Cytometry A., Aug. 2008, vol. 73, No. 8, pp. 693-701.
Chandran et al., "Gene expression profiles of prostate cancer reveal involvement of multiple molecular pathways in the metastatic process", BMC Cancer, Apr. 12, 2007, vol. 7, No. 64, pp. 1-21.
Chao et al., "Establishment of a Normal Hematopoietic and Leukemia Stem Cell Hierarchy", Cold Spring Harb. Symp. Quant. Biol., vol. 73, pp. 439-449, 2008, E-published Nov. 6, 2008.
Chattopadhyay et al., "Quantum Dot Semiconductor Nanocrystals for Immunophenotyping by Polychromatic Flow Cytometry", Nature Medicine, Aug. 2006, Published online Jul. 23, 2006, vol. 12, No. 8, pp. 972-977.
Chen et al., "Thrombopoietin Cooperates With FLT3-ligand in the Generation of Plasmacytoid Dendritic Cell Precursors From Human Hematopoietic Progenitors", Blood, Apr. 1, 2004, vol. 103, No. 7, pp. 2547-2553.
Desper et al., "Tumor Classification Using Phylogenetic Methods on Expression Data", Journal of Theoretical Biology, Jun. 21, 2004, vol. 228, Issue 4, pp. 477-496.
Eisen et al., "Cluster analysis and display of genome-wide expression patterns", Proc. Nat. Acad. Sci. USA, vol. 95, Dec. 1998, pp. 14863-14868.
Ellis et al., "flowCore: data structures package for flow cytometry data", Retrieved from: https://www.bioconductor.org/packages/release/bioc/vignettes/flowCore/inst/doc/HowTo-flowCore.pdf, Jan. 8, 2018, 33 pgs.
Filkov et al., "Analysis Techniques for Microarray Time-Series Data", Journal of computational Biology, Feb. 2002, vol. 9, No. 2, pp. 317-330.
Furey et al., "Support vector machine classification and validation of cancer tissue samples using microarray expression data", Bioinformatics, 2000, vol. 16, No. 102000, pp. 906-914.
Guha et al., "LPS Induction of Gene Expression in Human Monocytes", Cell Signal, 13(2):85-94, Feb. 2001.
Gupta et al., "Extracting Dynamics From Static Cancer Expression Data", IEEE/ACM Trans Comput Biol Bioinformatics, Apr.-Jun. 2008, vol. 5, pp. 172-182.
Herzenberg et al., "Interpreting Flow Cytometry Data: A Guide for the Perplexed", Nature Immunology, Jul. 2006, vol. 7, No. 7, pp. 681-685.
Huang et al., "Bayesian Inference of Genetic Regulatory Networks from Time Series Microarray Data Using Dynamic Bayesian Networks", Journal of Multimedia, Jun. 2007, vol. 2, No. 3, pp. 46-56.
Hystad et al., "Characterization of Early Stages of Human B Cell Development by Gene Expression Profiling", Journal of Immunology, Sep. 15, 2007, vol. 179, pp. 3662-3671.
Konishi et al., "Statistical Edge Detection: Learning and Evaluating Edge Cues", IEEE Transactions on Pattern Analysis and Machine Intelligence Archive, Jan. 2003, vol. 25, Issue 1, pp. 57-74.
Kotecha et al., "Web-Based Analysis and Publication of Flow Cytometry Experiments", Current Protocols in Cytometry, Jul. 2010, vol. 53, Unit 10.17.1-10.17.24, 40 pgs.
Lee et al., "Dimensionality Reduction and Clustering on Statistical Manifolds", Computer Vision and Pattern Recognition, 2007, CVPR 2007, IEEE Conference, Jun. 2007, 7 pages.
Lo et al., "Automated Gating of Flow Cytometry Data Via Robust Model-Based Clustering", Cytometry A., Apr. 2008, Published online Feb. 28, 2008, vol. 73, No. 4, pp. 321-332.
Magwene et al., "Reconstrucing the temporal ordering of biological samples using microarray data", Bioinformatics, May 1, 2003, vol. 19, No. 7, pp. 842-850.
Mandel et al., "Transcription control of early b cell differentiation", Current Opinion in Immunology, Apr. 2010, Available online Feb. 9, 2010, vol. 22, Issue 2, pp. 161-167.
Margolin et al., "ARACNE: An Algorithm for the Reconstruction of Gene Regulatory Networks in a Mammalian Cellular Context", BMC Bioinformatics, Mar. 20, 2006, vol. 7 (Supp 1), No. S7, 15 pgs.
Monti et al., "Consensus Clustering: A Resampling-Based Method for Class Discovery and Visualization of Gene Expression Microarray Data", Machine Learning, 2003, vol. 52, pp. 91-118.
Murphy, R.F., "Automated Identification of Subpopulations in Flow Cytometric List Mode Data Using Cluster Analysis", Cytometry, Jul. 1985, vol. 6, No. 4, pp. 302-309.
Nash-Williams, "Edge-Disjoint Spanning Trees of Finite Graphs", Journal of the London Mathematical Society, 1961, vol. 36, No. 1, pp. 445-450.
O'Neill et al., "Neural network analysis of lymphoma microarray data: prognosis and diagnosis near-perfect", BMC Bioinformatics, Apr. 10, 2003, vol. 4, No. 13, 12 pgs.
Park et al., "Network-Based Inference of Cancer Progression from Microarray Data", IEEE/ACM Transactions on Computational Biology and Bioinformatics, Apr.-Jun. 2009, vol. 6, pp. 200-2012.
Pettie et al., "An Optimal Minimum Spanning Tree Algorithm", Journal of the ACM, 49:49-60, 1999.
Pyne et al., "Automated High-Dimensional Flow Cytometric Data Analysis", PNAS, May 26, 2009, vol. 106, No. 21, pp. 8519-8524.
Qiu et al., "Discovering Biological Progression Underlying Microarray Samples", PLoS Computational Biology, Apr. 14, 2011, vol. 7, Issue 4, e1001123, 11 pgs.
Qiu et al., "Fast Calculation of Pairwise Mutual Information for Gene Regulatory Network Reconstruction", Computer Methods and Programs in Biomedicine, May 1, 2009, vol. 94, No. 1, pp. 177-180.
Qiu et al., "Simultaneous Class Discovery and Classification of Microarray Data Using Spectral Analysis", Journal of Computational Biology, Aug. 2009, vol. 16, No. 7, pp. 935-944.
Sacchi et al., "Precedence Temporal Networks to represent temporal relationships in gene expression data", Journal of Biomedical Informatics, Jun. 10, 2007, vol. 40, pp. 761-774.
Schaffalitzky et al., "Multiview-matching for unordered image sets, or "How do I organize my holiday snaps?"", ECCV '02 Proceedings of the 7th European Conference on Computer Vision—Part I, May 28-31, 2002, pp. 414-431.
Storey et al., "Significance analysis of time course microarray experiments", PNAS, Sep. 6, 2005, vol. 102, No. 36, pp. 12837-12842.
Subramanian et al., "Gene set enrichment analysis: A knowledge-based approach for interpreting genome-wide expression profiles", PNAS, Oct. 25, 2005, vol. 102, No. 43, pp. 15545-15550.
Tavazoie et al., "Systematic Determination of Genetic Network Architecture", Nature Genetics, Jul. 1999, vol. 22, pp. 281-285.
Tusher et al., "Significance analysis of microarrays applied to the ionizing radiation response", PNAS, Apr. 24, 2001, vol. 98, No. 9, pp. 5116-5121.
Tutte, "On the problem of decomposing a graph into n connected factors", Journal of the London Mathematical Society, Jan. 1, 1961, pp. 221-230.
Van Lochem et al., "Immunophenotypic Differentiation Patterns of Normal Hematopoiesis in Human Bone Marrow: Reference Patterns for Age-Related Changes and Disease-Induced Shifts", Cytometry B, Jul. 2004, vol. 60, No. 1, pp. 1-13.
Walther et al., "Automatic Clustering of Flow Cytometry Data with Density-Based Merging", Advances in Bioinformatics, 2009, 7 pgs.
Wan et al., "HAMSTER: visualizing microarray experiments as a set of minimum spanning trees", Source Code for Biology and Medicine, Nov. 20, 2009, vol. 4, No. 8, 18 pgs.
Whitfield et al., "Identification of Genes Periodically Expressed in the Human Cell Cycle and Their Expression in Tumors", Molecular Biology of the Cell, Jun. 2002, vol. 13, pp. 1977-2000.
Wu et al., "Efficient and Accurate Construction of Genetic Linkage Maps from the Minimum Spanning Tree of a Graph", PLoS Genetics, Oct. 10, 2008, vol. 4, Issue 10, e1000212, pp. 1-11.

(56) References Cited

OTHER PUBLICATIONS

Xu et al., "Clustering gene expression data using a graph-theoretic approach: an application of minimum spanning trees", Bioinformatics, Apr. 1, 2002, vol. 18, pp. 536-545.
Yip et al., "Gene network interconnectedness and the generalized topological overlap measure", BMC Bioinformatics, Jan. 24, 2007, vol. 8, No. 22, 14 pgs.
Zeng et al., "Feature-guided clustering of multi-dimensional flow cytometry datasets", ScienceDirect, Journal of Biomedical Informatics, 2007, available online Jun. 27, 2006, pp. 325-331.
Zhang et al., "A General Framework for Weighted Gene Co-Expression Network Analysis", Statistical Applications in Genetics and Molecular Biology, 2005; vol. 4, Article 17, 11 pgs.
Zhou et al., "From sample similarity to ensemble similarity: Probabilistic distance measures in reproducing kernel Hilbert space", IEEE Transactions on Pattern Analysis and Machine Intelligence, Jun. 2006, vol. 28, No. 6, 34 pgs.
Zhu et al., "Network Constrained clustering for gene microarray data", Bioinformatics, Sep. 1, 2005, vol. 21, No. 21, pp. 4014-4020.

\* cited by examiner

*FIG. 10* (Simulated Ground Truth Data)

SPANNING-TREE PROGRESSION ANALYSIS OF DENSITY-NORMALIZED EVENTS (SPADE)

CROSS REFERENCE TO RELATED APPLICATIONS

This application is a continuation-in-part of Ser. No. 13/338,237, filed 27 Dec. 2011, which claims the benefit of 61/427,467, filed 27 Dec. 2010, and claims priority from provisional patent application 61/449,557, filed 4 Mar. 2011 and incorporated herein by reference for all purposes.

This invention was made with Government support under contract CA112973 awarded by the National Institutes of Health. The Government has certain rights in this invention.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

SOURCE CODE ELECTRONIC APPENDIX

This application is being filed with an electronic appendix. These appendices and all other papers filed herewith, including papers filed in any attached Information Disclosure Statement (IDS), are incorporated herein by reference. The appendix contains further examples and information related to various embodiments of the invention at various stages of development and sets out selected source code extracts from a copyrighted software program, owned by the assignee of this patent document, which manifests the invention.

FIELD OF THE INVENTION

The present invention relates to sample collection and analysis and systems for performing biological analysis.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Flow cytometry (FC) systems are standard pieces of equipment in various biological investigation settings. A typical FC experiment collects data from thousands of cells, with each cell labeled with a number of detectable markers usually indicating specific cell-surface proteins, but also potentially labeling other cellular features. Because FC systems can quickly gather features from thousands to hundreds of thousands of cells, an FC experiment can quickly gather huge datasets from cell samples. Such analysis has accelerated many types of investigation.

FC analysis systems can include a number of components for preparing cells or samples, capturing feature data from cells, sorting cells, and providing one or more outputs or taking further actions in response to the data. While methods and components of such systems vary, operation of automated or semi-automated FC data collection and analysis systems is extremely well-know in various biologic, medical, and forensic fields. While FCs are most commonly used today to collect features related to cell-surface proteins or receptors, FC technology is increasingly being use or considered for other applications, such as protein analysis, chemical analysis, etc.

A critical component of FC systems are computational tools that are applied to the features collected by the systems. Because a single FC experiment can include readings from thousands of cells, with up to about 30 features in recent FC systems available for each cell samples, automated compilation and analysis of FC data is an important component of FC data systems. This analysis may be performed by information enabled laboratory equipment used to gather FC data or the laboratory equipment can collect and store the feature data in a digital recording medium and those data can be read and processed at a later time by FC analysis systems. A number of data sets from FC experiments are published and are used to evaluate and validate new methods for analysis of FC feature data.

Multiparametric single-cell analysis has advanced understanding of diverse biological and pathological processes including cellular differentiation, intracellular signaling cascades and clinical immunophenotyping. Analysis by flow cytometry in increasingly used to analyze intracellular markers (e.g., phosphorylated proteins) for drug targeting and the identification of rare stem cell populations. Current flow cytometers typically provide simultaneous single-cell measurements of up to 12 fluorescent parameters in routine cases, and analysis of up to 19 parameters has been reported [1]. Recently, a commercially available next-generation mass cytometry platform (CyTOF™, DVS Sciences Inc., Toronto, ON, Canada) has become available and that allows routine measurement of 30 or more single-cell parameters [2]. Despite increasing research in cytometric analysis and the technological advances in acquiring an increasing number of parameters per single cell, methods for analyzing multidimensional single-cell data remain inadequate.

Flow cytometry simultaneously measures multiple proteins of individual cells. In typical flow cytometry studies, surface proteins are labeled with fluorescent dyes to generate fluorescent signals. Multiple colors of fluorescent labels can be used to stain multiple markers. After staining, individual cells generally are held in a thin stream of fluid and then passed through one or more laser detectors, which give measurements of size, granularity, and intensities of the fluorescent labels on a single cell basis. Flow cytometry is able to process up to 7000 cells per second, generating large datasets containing measurements of multiple protein markers on a large number of cells. Thus, Flow cytometry captures the heterogeneity of biological systems by providing multiparametric measurements of individual cells. Traditional analysis of cytometry datasets is a subjective process that requires intimate familiarity with the biological system.

Thus, in various fields, methods for exploring or analyzing data sets where a large number of samples (e.g., typically about $10^3$ to about $10^8$ cell samples, though any number of samples can be analyzed) are each characterized by a moderate number of features (e.g., typically 5 to about 30) remain limited.

Traditional methods for flow cytometry data analysis are often subjective and labor-intensive processes that require expert knowledge of the underlying cellular phenotypes. One common but cumbersome step is the selection of subsets of cells in a process called gating [3]. A gate is a region, defined in a biaxial plot of two measurements, which is used to select cells with a desired phenotype for downstream analysis. Gates are either manually drawn, for example, using software such as FlowJo (www(.)treestar(.)com/), FlowCore [4], or automatically defined by clustering algorithms [5, 6, 7, 8, 9, 10]. Manual gating is highly subjective and dependent on the investigator's knowledge and interpretation of the experiment. Automatic gating algorithms cluster cells by optimizing the objective that cells in the same cluster be more similar to each other than cells from other clusters. Because these algorithms strive to define maximally different clusters, they often miss the underlying continuity of phenotypes (progression) that is inherent in cellular differentiation [11].

Furthermore, optimization objectives of most automatic gating algorithms are predisposed to capture usually the most abundant cell populations, while rare cell types, such as stem cells, are either excluded as outliers or absorbed by larger clusters. Some algorithms, such as a recent approach for automated gating termed SamSPECTRAL provides a solution for rare cell type identification [12].

Traditional cytometry data analysis methods also commonly suffer from limitations in scalability and visualization with increasing numbers of measurements per single cell. These limitations are more acute as the data dimensionality increases. Currently, to fully visualize an m-dimensional flow dataset, ½ m*(m−1) biaxial plots are needed, where each biaxial plot displays the correlation of only two markers at one time. It is difficult to comprehend the correlations among three or more markers from a series of biaxial plots. One recent approach that partly addresses the scalability issue is the probability state model, implemented in the Gemstone™ software package (such as from Verity Software House, Inc.). This approach rearranges cells into a non-branching linear order, according to investigator's expert knowledge of how known markers behave during the progression underlying the measured cell population [13]. Because cells are ordered in a non-branching fashion, a new model is constructed for each mutually exclusive cell type (e.g., T cells, B cells).

Flow cytometry data can be displayed using one-parameter histograms or two-parameter scatter plots, based on which gating is performed. A gate is a user-defined region either in the one-parameter histograms or in the two-parameter scatter plots, which can be used to exclude irrelevant cells and select subpopulation of cells of interest. After gating, subsequent analyses are performed to identify cell subpopulations and relevant surface markers, based on the two-parameter scatter plots.

One recent advancement that partly addresses the issue of parameter scalability and visualization is a ribbon plot of cells arranged into a linear order, for example as implemented in the "Probability State Model" of the Gemstone® software. This approach rearranges cells into a linear order according to user's expert inputs. Given a flow cytometry dataset containing tens of thousands of cells, this approach asks the user to specify one marker and how it changes during the progression underlying the data. Cells are then ordered linearly according to the change of the marker specified by the user. The user is able to refine this order by sequentially specifying more markers and their changes. Once the cells are ordered, changes of all the measured markers can be visualized in one single figure, a "ribbon plot." FIG. 1 illustrates an example of a ribbon plot of linearly ordered cells used to illustrate and analyze B cell progression according to the prior art. Although this approach scales well as the number of parameters increases, it has two disadvantages. First, it requires a user's knowledge of which markers change and how these markers change during the progression underlying the measured cell population. The approach is not able to automatically identify relevant markers or discover an unknown progression order or cellular differentiation or hierarchy. Second, differentiation and branching underlying the measured cell population cannot be represented by a linear order of the cells. Therefore, if the user does not have prior knowledge about the progression underlying the measured cell population, or if there exists differentiation and branching, the approach fails.

OTHER REFERENCES

The following additional references may provide background and other information regarding the state of the art. Applicant makes no representation as to the effective dates of these references.

SUMMARY

The present invention (a specific implementation of which is at times herein referred to as SPADE™) provides advantages over or is used in combination with existing approaches for analyzing flow cytometry data cellular sample data. The invention has applications in other data sets, as described elsewhere herein. The invention provides an analysis and output grouping multiple cell sample types in a branched hierarchical tree structure that is constructed without requiring the user to define a known cellular ordering. Thus, the invention simultaneously provides a form of automated gating without sacrificing the representation of rare cell types. Moreover, the invention according to specific embodiments provides a visual output to a user that illustrates how measured features (e.g., markers or other features) behave across the entire cellular hierarchy, not just across selected cell types.

In specific example embodiments, the invention provides a computational algorithm to discover the progression or hierarchy among thousands of samples (e.g., cells), based on multidimensional data generally captured for on single samples, as measured, for example, by flowcytometry. When multiple feature measurements (e.g., single-cell molecular data measures) are made across thousands of cells, the invention according to specific embodiments (1) enables an easy visualization of this high-dimensional molecular data, (2) facilitates selection of subpopulations of interest for further analysis of their molecular properties ("gating"), (3) determines or predicts a progressive relationship underlying the subpopulations that define lineages and/or hierarchy of progression and differentiation, (4) identifies the features (e.g., molecular markers) that drive or are most associated with this underlying progression, and (5) discovers uncharacterized features that are highly relevant to the progression and hierarchy defined by well characterized features. The invention according to specific embodiments can be generalized to various multidimensional datasets.

FIG. 2 illustrates a flowchart of a example computational frameworks for discovering progression underlying multi-dimensional data (e.g., flow cytometry data) according to specific embodiments of the invention. As shown in the figure, the method clusters the cells, and then connects the cell-clusters in a graph to identify the progression. One embodiment uses an iterative agglomerative approach for clustering, although other clustering approaches can be used. One embodiment further uses minimum spanning trees to connect the clusters based on a pre-selected set of features (e.g., markers) that are known to define a cellular progression or hierarchy.

When features that define the hierarchy are not known, the invention further optionally uses a novel statistical method to discover the relevant features while simultaneously discovering the hierarchy. The hierarchy may describe a lineage of cellular differentiation or other forms of biological cellular progression, including disease progression and treatment response. The technical details and advantages of the present invention are further described in the context of its applications and examples.

A variety of prior comparative analyses have been applied to analyze high-throughput biology data. The focus of most existing methods is to identify the difference between pre-defined sample groups (cell subpopulations), while the difference among samples within the same group is ignored. The present invention provides a method to analyze and identify the difference and progression relationship among samples both within and between sample groups. The present invention represents multidimensional data using a progression tree that connects clusters of samples. This representation facilitates gating, discovery of progression and differentiation hierarchy, and discovery of correlation of uncharacterized features with respect to the identified progression tree.

The present invention, in specific embodiments, involves flow cytometry analysis methods and systems for analyzing and displaying or otherwise presenting a progression or relationship model for a number of samples where each sample is characterized by a number of detected features. According to specific embodiments, at least some of the features are expected to vary coherently according to a progression or relationship underlying the samples. The invention provides methods and systems for both finding the progression or relationship among the samples and for determining which of the many features are relevant to the progression. Systems and methods of the invention can operate using a logic processor associated with a flow cytometry or other relevant analysis system and can operate on both newly collected data and on stored data.

The present invention, in specific embodiments, more generally involves methods and systems for analyzing and displaying or otherwise presenting or outputting a progression or relationship model for a number of samples where each sample is characterized by a number of features, at least some of which are expected to vary according to the progression or relationship of the samples. A sample can more generally represent one or more of various objects or concepts or groups under study (such as cells, tissues, organisms, traded stocks or securities, people, etc.) For purposes of this discussion, a feature can represent one to a relative large number of measurements or values that characterize a sample.

Example implementations, including implementations used for demonstration and experimentation, are referred to at times herein as a Spanning-Tree Progression Analysis of Density-Normalized Events™ (SPADE™) system and/or method. One particular field of interest is to discover patterns of biological progression underlying data samples of gene expression features, protein expression features, cell surface markers or other biological markers. An illustrative biological implementation according to specific embodiments of the invention assumes that individual samples are related by an unknown biological process or hierarchy (e.g., differentiation, development, cell cycle, disease progression, cell transformation (fertilization, meiosis, mitosis, apoptosis, etc.) and that each sample is representative of an unknown point along the progression of that process. The invention, in general, aims to organize the samples in a manner that reveals the underlying relationships and also identify the features or sets of features (e.g., cell-surface markers, gene or protein expressions) that are responsible for that progression.

In specific embodiments, the invention may be viewed as a novel tool for identifying relationships or orderings of samples and which features are important for determining those relationships. The invention provides a likely progression or hierarchy underlying a set of samples of flow cytometry data and identifies candidate features (e.g., markers, surface proteins, genes or other factors) that regulate or are associated with that progression. In more general terms, SPADE can identify relationships and relevant features for sample sets with a large number of samples and a high dimensionality of features that both determines how samples are related to each other (e.g., a linear or branched progression) and which features are most likely important in that interrelation of samples.

As discussed above, methods and systems of the invention have applications other than FC data analysis or analysis of other biologic systems such as microarray, blot analysis, proteomics analysis, etc. The invention can be applied to a variety of high-dimensional feature measurements, including genomic, proteomic, population, economic, chemical, astrophysics, particle physics, and image-based data.

In addition, the invention has applications to other analysis of large datasets. Such datasets can include a feature set collected for a large number of consumers with regard to decisions to make certain purchases, the progression of citizens in utilization of government resources or services, progression of individuals under criminal justice supervision to either rehabilitation or recidivism, or other instances where it is desired to analyze very large data sets of samples to determine progression from one state to another of objects those samples represent.

As one example, the invention can be used to analyze certain economic actors. Consider an analysis a large number of companies or stocks in a stock market to determine relevant groupings Each stock represents a company that can be modeled as being at some point in a progression or differentiation from start up, to going public, to becoming profitable and a blue chip stock, to becoming part of a stock bubble, or to going bankrupt. Thousands of stocks may be analyzed using a set of features for each stock at a given point of time. In this analysis, the invention would attempt to find a hierarchy of large groupings of stocks as they progressed through relevant stages of a business cycle. The invention would attempt to both identify progressions and differentiations and feature that are important in determining progressions of stocks. Of course, there may be sample sets with feature sets that are analyzed by the invention that in fact have no progression relationship that is supported by the measured features. In such a case, the invention can provide a negative output, indicating that no likely progression relationships could be found.

The invention, as far as the inventors are aware, is unique in its ability to simultaneously reveal a hierarchy or progression from a large number of cells and reveal features (e.g., surface markers) that are associated with the progression, without prior knowledge or manual selection of groups of cells for analysis (e.g., gating).

While aspects and implementations of the invention will vary according to particular applications (e.g., population or economic analysis versus biologic progression analysis), the invention is best described and understood by considering a number of specific example applications. These example applications are taken from the field of biologic flow cytometry data analysis and some experimental results are discussed.

The invention and various specific aspects and embodiments will be better understood with reference to the following drawings and detailed descriptions. In some of the drawings and detailed descriptions below, the present invention is described in terms of the important independent embodiment of a system operating on a digital device or data network. This should not be taken to limit the invention, which, using the teachings provided herein, can be applied to other situations, such as cable television networks, wireless networks, etc. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

It is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems and/or methods that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Java-script, HTML, XML, dHTML, assembly or machine code programming, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

All references, publications, patents, and patent applications cited herein are hereby incorporated by reference in their entirety for all purposes. All documents, data, or other written or otherwise available material described or referred to herein, is herein incorporated by reference. All materials in any IDS submitted with this application are hereby incorporated by reference.

When used herein, "the invention" should be understood to indicate one or more specific embodiments of the invention. Many variations according to the invention will be understood from the teachings herein to those of skill in the art.

OTHER FEATURES & BENEFITS

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

REFERENCES

[1] P. Chattopadhyay, D. Price, T. Harper, M. Betts, J. Yu, E. Gostick, S. Perfetto, P. Goepfert, R. Koup, S. De Rosa, M. Bruchez, and M. Roederer. Quantum dot semiconductor nanocrystals for immunophenotyping by polychromatic flow cytometry. Nature Medicine, 12 (8):972-977, 2006.

[2] D. R. Bandura, V. I. Baranov, O. I. Ornatsky, A. Antonov, R. Kinach, X. Lou, S. Pavlov, S. Vorobiev, J. E. Dick, and S. D. Tanner. Mass cytometry: Technique for real time single cell multitarget immunoassay based on inductively coupled plasma time-of-flight mass spectrometry. Analytical Chemistry, 81 (16):6813-6822, 2009. 11

[3] L. Herzenberg, J. Tung, W. Moore, L. Herzenberg, and D. Parks. Interpreting flow cytometry data: a guide for the perplexed. Nat. Immunol, 7 (7):681-685, 2006.

[4] B. Ellis, P. Haaland, F. Hahne, N. Le Meur, and N. Gopalakrishnan. Flowcore: basic structures for flow cytometry data. R package version 1.10.0.

[5] R. F. Murphy. Automated identification of subpopulations in flow cytometric list mode data using cluster analysis. Cytometry, 6 (4):302-309, 1985.

[6] K. Lo, R. Brinkman, and R. Gottardo. Automated gating of flow cytometry data via robust model-based clustering. Cytometry A., 73 (4):321-332, 2008.

[7] M. Boedigheimer and J. Ferbas. Mixture modeling approach to flow cytometry data. Cytometry A., 73 (5): 421-429, 2008.

[8] C. Chan, F. Feng, J. Ottinger, D. Foster, M. West, and T. Kepler. Statistical mixture modeling for cell subtype identification in flow cytometry. Cytometry A., 73 (8): 693-701, 2008.

[9] G. Walther, N. Zimmerman, W. Moore, D. Parks, S. Meehan, I. Belitskaya, J. Pan, and L. Herzenberg. Automatic clustering of flow cytometry data with density-basedmerging. Advances in Bioinformatics, 2009.

[10] S. Pyne, X. Hu, K. Kang, E. Rossin, T. Lin, L. Maier, C. Baecher-Allan, G. McLachlan, P. Tamayo, D. Hafler, P. De Jager, and J. Mesirov. Automated high-dimensional flow cytometric data anlysis. PNAS, 106 (21):8519-8524, 2009.

[11] E. G. van Lochem, V. H. J. van der Velden, H. K. Wind, J. G. to Marvelde, N. A. C. Westerdaal, and J. J. M. van Dongen. Immunophenotypic differentiation patterns of normal hematopoiesis in human bone marrow: Reference patterns for age-related changes and disease-induced shifts. Cytometry B, 60B:1-13, 2004.

[12] H. Zare, P. Shooshtari, A. Gupta, and R. Brinkman. Data reduction for spectral clustering to analyze high throughput flow cytometry data. BMC Bioinformatics, 11 (1):403, 2010.
[13] B. C. Bagwell. Probability state models. U.S. Pat. No. 7,653,509, January 2010.
[14] S. C. Bendall, E. F. Simonds, P. Qiu, E. D. Amir, P. O. Krutzik, R. Finck, R. V. Bruggner, R. Melamed, O. I. Ornatsky, R. S. Balderas, S. K. Plevritis, K. Sachs, D. Pe'er, S. D. Tanner, 12 and G. P. Nolan. Single cell mass cytometry of differential immune and drug responses across the human hematopoietic continuum. submitted to Science, 2010.
[15] D. Bryder, D. j. Rossi, and I. L. Weissman. Hematopoietic stem cells: The paradigmatic tissuespecific stem cell. Am J Pathol, 169 (2):338-346, 2006.
[16] M. P. Chao, J. Seita, and I. L. Weissman. Establishment of a normal hematopoietic and leukemia stem cell hierarchy. Cold Spring Harb Symp Quant Biol, 73:439-449, 2008.
[17] J. D. Ashwell. The many paths to p38 mitogen-activated protein kinase activation in the immune system. Nature Reviews Immunology, 6:532-540, 2006.
[18] M. Guha and N. Mackman. Lps induction of gene expression in human monocytes. Cellular Signalling, 13 (2):85-94, 2001.
[19] W. Chen, S. Antonenko, J. M. Sederstrom, X. Liang, A. S. Chan, H. Kanzler, B. Blom, B. R. Blazar, and Y. J. Liu. Thrombopoietin cooperates with flt3-ligand in the generation of plasmacytoid dendritic cell precursors from human hematopoietic progenitors. Blood, 103 (7):2547-2553, 2004.
[20] P. Qiu, A. J. Gentles, and S. K. Plevritis. Discovering biological progression underlying microarray samples. submitted to PLoS Computational Biology, 2010.
[21] N. Kotecha, P. O. Krutzik, and J. M. Irish. Web-based analysis and publication of flow cytometry experiments. Current Protocols in Cytometry, 53:10.17.1-10.17.24, 2010.
[22] S. Pettie and V. Ramach. An optimal minimum spanning tree algorithm. Journal of the ACM, 49:49-60, 1999.

BRIEF DESCRIPTION OF THE FIGURES

The patent or application file contains at least one drawing executed in color. Copies of this patent or patent application publication with color drawing(s) will be provided by the Office upon request and payment of the necessary fee.

DESCRIPTION OF SPECIFIC EMBODIMENTS

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein.

According to specific embodiments of the invention, the invention involves a novel computational approach, at times referred to as Spanning-tree Progression Analysis of Density-normalized Events (SPADE™), to analyze the heterogeneity in flow data, without requiring prior knowledge or hypotheses about the underlying hierarchy. SPADE enables several novel approaches for cytometric analysis, including merging of overlapping reagent panels and direct comparison of feature intensities across multiple datasets. In various datasets (e.g., conventional and next-generation cytometry data of mouse and human bone marrow), the invention can detect a cellular hierarchy that accords well with known well-described patterns of hematopoiesis. In experiments, using the next-generation cytometry data, the invention defined a functionally distinct cell population, inferred to be NK cells, without using any NK-specific markers. The invention can map intracellular signal activation e.g., across the landscape of human hematopoietic development. SPADE is a versatile tool for analysis of flow cytometry, facilitating automated comparison of functional markers and identification of rare or malignant cell populations.

As an example, a flow cytometry dataset generally contains measurements of multiple markers or features (e.g., 2 to 20 to 31 or more) for a large number of cells (e.g., about $10^3$ to $10^8$). Such a dataset can be viewed as a point cloud of samples (e.g., cells) in high-dimensional space defined by the measured features. An hierarchical agglomerative clustering procedure is one method according to specific embodiments that can be used to group the data point samples into clusters. For the sake of simplifying the description, the data points in this examples represent cells and are described as such. Thus, in the description below a "cell" is synonymous with a data point in the analysis.

Figure 1:
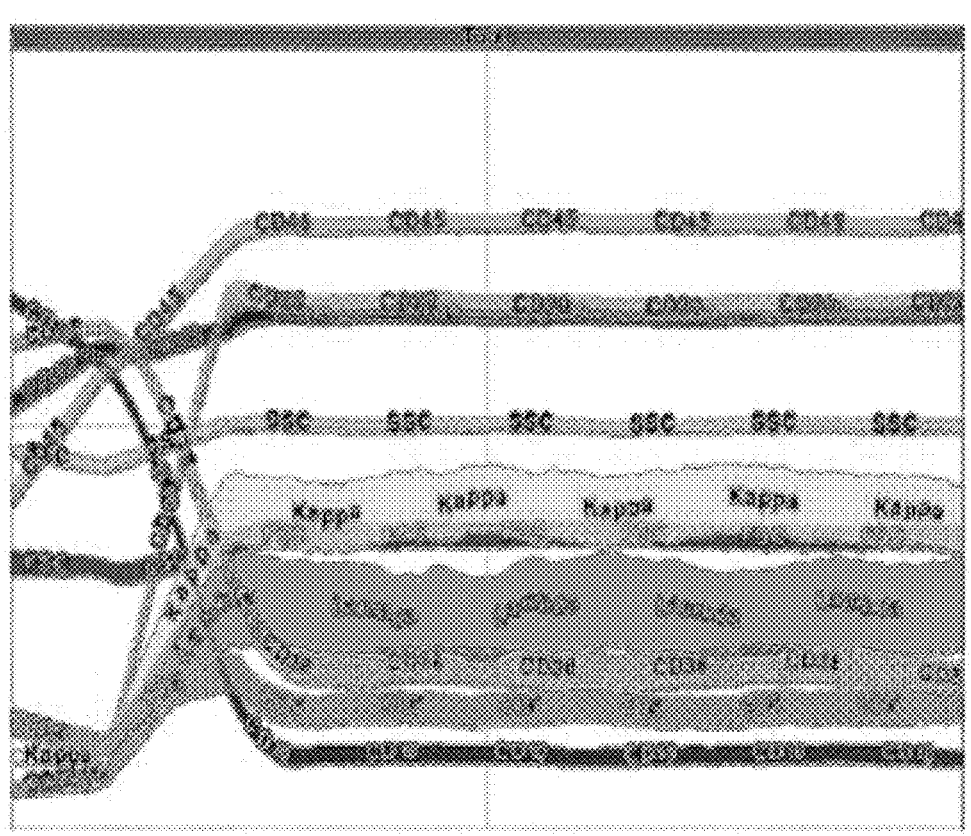
FIG. 1 illustrates an example of a ribbon plot of linearly ordered cells used to illustrate and analyze B cell progression according to the prior art.
Figure 2:
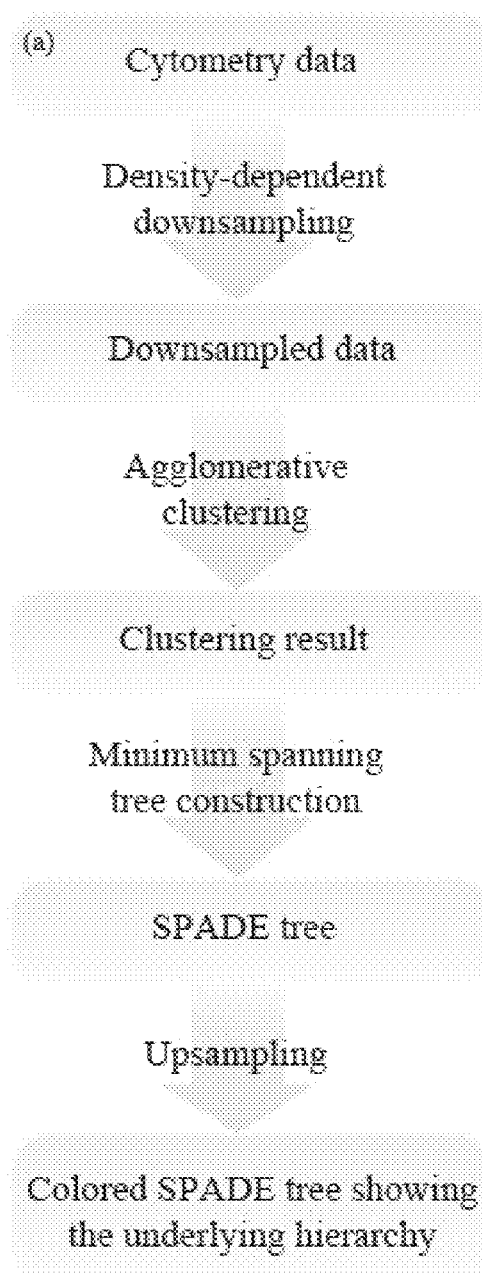
FIG. 2 illustrates a flowchart of a example computational frameworks for discovering progression underlying multidimensional data (e.g., flow cytometry data) according to specific embodiments of the invention.

FIG. 2 illustrates a flowchart of a example computational frameworks for discovering progression underlying multi-dimensional data (e.g., flow cytometry data) according to specific embodiments of the invention. At a general level the invention according to specific embodiments can be understood as comprising three primary steps or components: (1) density-dependent downsampling, (2) agglomerative clustering, and (3) minimum spanning tree construction. These steps are explained below in general terms. To further elucidate the invention according to specific embodiments, the method steps are also described below with reference to a particular illustrative example, which is denoted herein as Example 1. After the general description, applications of the invention to other example datasets are provided.

Figure 3:
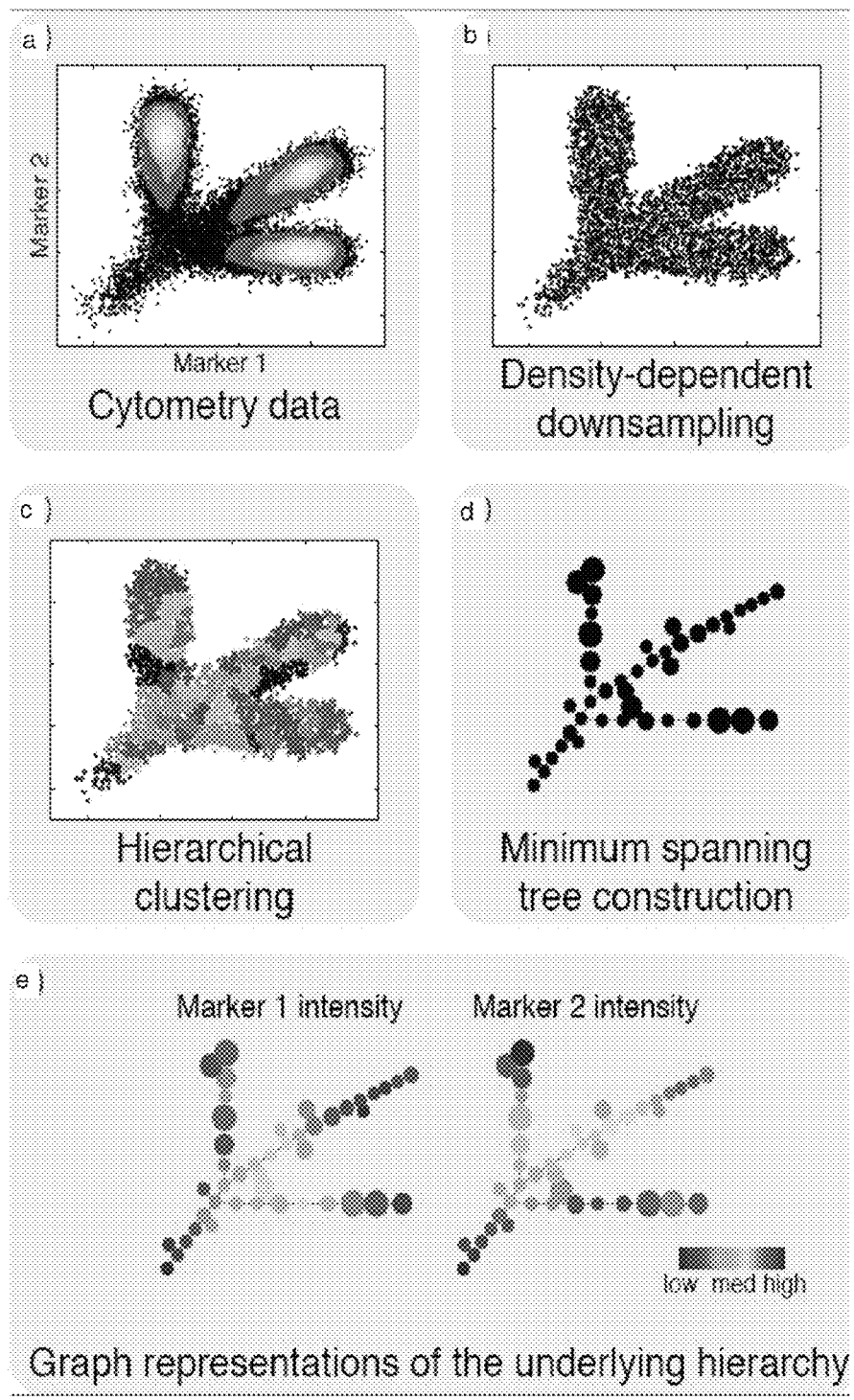
FIG. 3 illustrate a simulated illustrative example using just 2 parameters for performing clustering analysis of datasets and example output results of method steps according to specific embodiments of the invention.

FIG. 3 illustrate a simulated illustrative example using just 2 parameters for performing clustering analysis of datasets and example output results of method steps according to specific embodiments of the invention. An example application of the invention to a very simple, 2-marker, flow-cytometry analysis is illustrated by the diagrams shown in FIG. 3. The invention will be described with reference to this figure to provide an initial understanding of the invention. Examples that are more complex are provided thereafter.

FIG. 3a illustrates a 2-feature (or parameter) simulated flow cytometry dataset using a conventional scatter plot in which the underlying differentiation hierarchy started from a rare root cell type and differentiated gradually into three abundant cell types. FIG. 3b illustrates application of density-dependent downsampling according to specific embodiments, which heavily downsampled the abundant cell types, while the rare root cell type was preserved. More importantly, the shape of the point cloud was not altered by the downsampling scheme. FIG. 3c illustrates application of an agglomerative algorithm used to cluster the downsampled cells. Adjacent clusters are drawn in alternating colors. Since the downsampling step made the abundant and rare cell types relatively equally represented, the rare root cells formed their own clusters. FIG. 3d illustrates construction of a tree that connected the cell clusters. The topology of the MST reflects the shape of the point cloud, which retraced the underlying differentiation hierarchy. FIG. 3e illustrates nodes color-coded to show the median intensity of the protein markers, allowing the behaviors of the two markers to be visualized across the entire differentiation hierarchy, according to specific embodiments of the invention.

Density-Dependent Downsampling

The invention according to specific embodiments models a dataset as a point cloud in a high-dimensional space, defined by the measured features (or markers). Each point in the cloud is one cell or one sample, and the number of dimensions is generally determined by the number of measured features. The shape of this point cloud represents a continuum of the progression and differentiation hierarchy underlying the data. Parts of the point cloud that correspond to abundant cell or sample types have high density, while low density regions of the point cloud correspond to rare cell types and cells in transition between abundant cell types. Most existing clustering algorithms rely on the density variation to identify clusters of abundant cell types [5, 6, 7, 8, 9]. In contrast, the invention performs density-dependent downsampling to remove the density variation in order to better identify rare cell or sample types. Downsampling the data in density-dependent fashion in the high dimensional space provides that abundant and rare cell types are relatively equally represented, and rare cell types are more likely to form their own clusters.

In one example implementation, In order to perform density-dependent downsampling, the invention first estimates the local high dimensional density for each cell. The local density of a cell i ($LD_i$) is defined as the number of cells within a user-defined n-dimensional neighborhood of this cell. The size of the neighborhood is chosen such that most cells have at least one neighbor. According to specific embodiments, the user or investigator chosen parameters target density (TD) and outlier density (OD), the invention downsamples each cell i with the following probability:

$$\text{prob}(\text{remove cell } i) = \begin{cases} 1, & \text{if } LD_i \leq OD \\ 0, & \text{if } OD < LD_i \leq TD \\ 1 - \dfrac{TD}{LD_i}, & \text{if } LD_i > TD \end{cases}$$

Therefore, cells whose local densities are between the outlier density and the target density are not downsampled. Cells in high-density regions are heavily downsampled such that their local densities reduce to approximately the target density after downsampling. The target density can be defined by the local density of the rare cell types of interest. For example, if the investigator is interested in finding a rare cell type that represents only 3% of the entire dataset, the target density is set to be the 3rd percentile of the local densities of all cells.

The target density can be defined by the local density of the rare cell types of interest. For example, if a user or investigator is interested in finding a rare cell type that represents only 3% of the entire dataset, the target density is set to be the 3rd percentile of the local densities of all cells. The simulated dataset in FIG. 3 contains 20,000 cells. In that example, OD and TD were chosen to be the 1st and 3rd percentiles of the local densities of all the cells. In this example, the invention downsampled the dataset to about 4000 cells. Although the size of the dataset was significantly reduced, most cells of the rare cell type remained after downsampling, and the shape of the point cloud was preserved.

Clustering Dataset Samples

After downsampling, the invention according to specific embodiments employs a variant of agglomerative hierarchical clustering algorithm to define cell clusters. Details of one example clustering procedure are as follows. At the beginning of the first iteration of the agglomerative clustering process, each cell in the point cloud is treated as its own cluster. One cell is randomly chosen and grouped with its nearest neighbor, defined by the Euclidean distance in the n-dimensional space. Then, another cell is randomly chosen from the remaining cells and grouped with its nearest neighbor, if the nearest neighbor has not already been grouped with other cells in the current iteration. After all the cells are examined (e.g., either chosen or grouped with other cells), the first iteration ends and the number of clusters is reduced by approximately half. The same procedure is repeated in the second iteration to further reduce the number of clusters by half. The iterative process continues until the number of remaining clusters reaches an investigator-defined threshold.

By way of further example, the details of one example clustering procedure are as follows: (1) A first iteration of the agglomerative clustering process starts from the point cloud of cells. One cell is chosen (either randomly, or according to a rule or preference, e.g., choosing the first cell or middle cell or $100^{th}$ cell in a data set) and grouped with its nearest neighbor, if the nearest neighbor has not already been grouped with any other cell in the current iteration. The nearest neighbor is identified using the Euclidean distance or other well defined distance metrics (e.g., L–1 distance, correlation, mutual information, etc.) or any other metrics or characteristics of interest in a clustering or grouping method. This distance is determined with respect with generally two or more measured features (e.g., markers or characteristics) of the data point. Features need not be equally weighed or scaled and thus some features or combination of features can have more affect on the distance determined for the data points than other features. (2) After generally all the cells are examined, a first iteration ends, and the number of points in the cloud is reduced by approximately half. (3) Then a second iteration starts to further reduce the number of clusters by half. (4) The iterative process continues until the number of remaining clusters reaches the number of desired cell clusters defined by the user.

The clustering procedure simplifies the point cloud, distilling it into abutting cell clusters that span the full space occupied by the original dataset. The scale of the simplification can be controlled by adjusting the number of clusters at the user's choice.

FIG. 3c illustrates results of the clustering of the downsampled cells. Adjacent clusters are shown in alternating colors for the purpose of illustration. In this example, about 40 clusters were formed. Since the downsampling step made the abundant and rare cell types relatively equally represented, the rare root cells formed their own clusters. This is one advantage to the down sampling procedure.

Construction of a Progression Tree or Graph (e.g., an MST) Connecting Cell-Clusters After the samples are grouped into clusters, a graph that connects the clusters is constructed to describe a hierarchy among the clusters, depicting the progression and differentiation underlying the data. This graph, or "progression tree", is represented by the minimum spanning tree (MST) constructed based on a relevant set of features.

The minimum spanning tree (MST) is an undirected acyclic graph that connects all the cell clusters with minimum number of edges (lines connecting the different nodes representing clusters or center points of the clusters) and minimum total edge length.

Based on measurements of a set of features, a fully connected undirected graph is constructed, where each node represents one cell cluster. The length of the edge that connects nodes i and j is defined as the Euclidean distance between the average measurements of clusters i and j. Then, the MST can be derived from the fully connected graph, for example using the Borůvka's algorithm.

Because the MST connects all the nodes using minimum total edge length, MST tends to connect cell clusters that are more similar to each other. Thus, MST reflects the geometry and progressive relationship of the cell clusters defined by the set of features, based on which the MST is constructed. Therefore, the name progression tree is used to denote the MST constructed from a set of features in flow cytometry data. The progression tree can be easily visualized in a two dimensional plane.

A progression tree constructed from the synthetic example is shown in FIG. 3d, where the edges represent the structure of the tree, and the size of each node is proportional to the logarithm of the number of cells in its corresponding cluster. Since the tree connected clusters that were close to each other to achieve the minimum total edge length, the resulting tree structure retraced the gradual change of feature intensities among the clusters, extending outward in three branches from the "root" population. Thus, the topology of the tree revealed the differentiation hierarchy underlying the synthetic dataset.

FIG. 3e illustrates a display output of a tree according to specific embodiments of the invention wherein nodes are color-coded to show the median intensity of the protein features, allowing the behaviors of the two features to be visualized across the entire differentiation hierarchy. Note that in this example, essentially all of the flowcytometry data of interest is displayed in a limited number of figures. One MST figure without feature indications showing the distance relationships of the nodes, and one identically shaped figure showing a color-coding for each feature of interest.

In further embodiments, the invention can be understood as a computer implemented method for visualizing or representing in a Euclidean space (e.g., 1, 2, or 3-dimensions), a data set in a non-Euclidean space (e.g., 4 or more dimensions). While a presently preferred embodiment uses 2-dimensional outputs, 3-dimensional outputs may also be provided in 3-dimensional displays according to specific embodiments of the invention.

Upsampling

To calculate the median intensity and other statistics of each cluster with high accuracy, SPADE performs "upsampling" by assigning each cell in the original dataset to one cluster. For each cell in the original dataset, SPADE finds its nearest neighbor in the downsampled data, and assigns this cell to the cluster that the nearest neighbor belongs to.

Example 2: Mouse Bone Marrow

Figure 4:
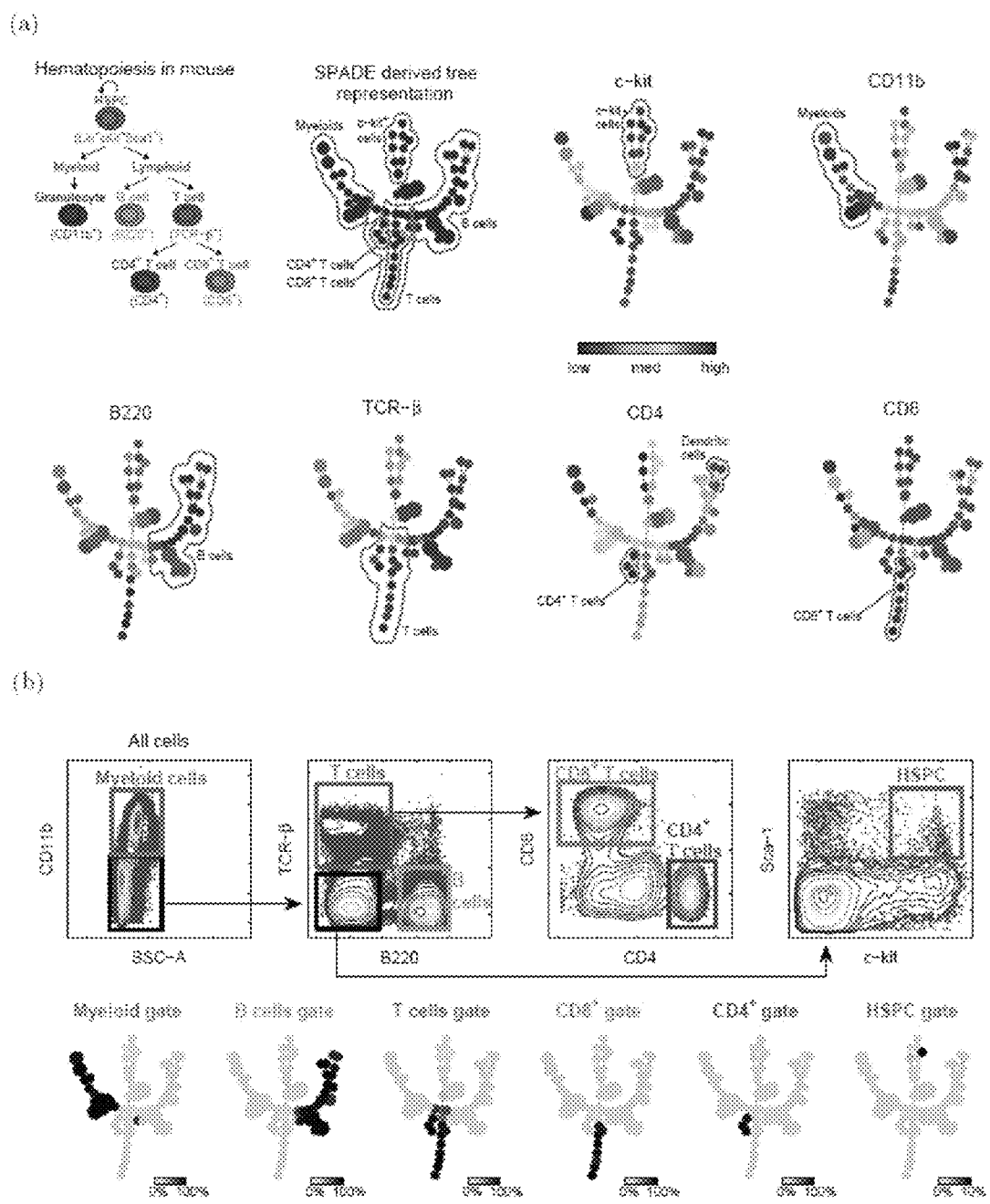
FIG. 4 illustrates outputs from the analysis according to the invention applied to mouse bone marrow data. (a) Simplified mouse hematopoietic hierarchy of mouse bone marrow, and the MST derived by SPADE. The MST was color-coded by median intensities of one individual marker, to show how markers behave across the MST. (b) Traditional gating analysis of the mouse bone marrow data. To illustrate the concordance between SPADE and gating, for each gated population, the SPADE-derived MST was drawn, where each node was color-coded by the percentage of gated cells in that node.

While the simplicity of the underlying 2-dimensional data set illustrated in FIG. 3 helps illustrate some aspects of the invention, the true power of the invention is further illustrated by considering a more complex data set illustrated in FIG. 4. FIG. 4 illustrates outputs from the analysis according to the invention applied to mouse bone marrow data. (a) Simplified mouse hematopoietic hierarchy of mouse bone marrow, and the MST derived by SPADE. The MST was color-coded by median intensities of one individual marker, to show how markers behave across the MST. (b) Traditional gating analysis of the mouse bone marrow data. To illustrate the concordance between SPADE and gating, for each gated population, the SPADE-derived MST was drawn, where each node was color-coded by the percentage of gated cells in that node.

This example demonstrates the invention's ability to detect a branched hierarchy underlying a heterogeneous population of real cells. The analysis was applied to conventional (8-parameter) flow cytometry data of normal mouse bone marrow, a well-defined biological system with multiple known developmental transition points.

FIG. 4a shows a representation of the known hematopoiesis hierarchy of a mouse bone marrow next to a 2-dimensional drawing of a 6-dimensional progression tree according to specific embodiments of the invention output for the six cell markers as indicated in the figure. In this example, the flow data is presented by a total of seven illustrations: one black MST figure without marker indications showing the distance relationships of the nodes, and one identically shaped figure showing a color-coding for each marker of interest. The various outline annotations indicating cell subpopulations in FIG. 4a are added to show the final results of the analysis. As above, after downsampling, a variant of agglomerative hierarchical clustering is used to define cell clusters, which are then connected by a progression tree revealing the skeleton of the point cloud. The progression tree is visualized in two-dimensions. The behavior of each marker is visualized simultaneously across the entire tree by color-coding the nodes with the marker's median intensity within each of the cell clusters. By navigating between trees color-coded with different markers, the investigator can associate branches with familiar 'landmark' cell types based on their understanding of the system. Once the structure of the tree is put in context, it becomes possible to identify new cell types, investigate the behavior of uncharacterized markers, and compare the response of functional markers to different experimental conditions.

FIG. 4b shows a representation of four conventional 2-dimensional scatter plots of the same data set shown in FIG. 4a. Because of the limitations of the 2-dimensional scatter plots, a total of 36 (6×6) scatter plots would be needed to represent all the possible pairings of the six markers. The gating shown by the rectangular outlines in FIG. 4b is conventionally done by a skilled technician or researcher, relying on knowledge of important markers, as discussed elsewhere herein. To illustrate the concordance between the invention and conventional gating, for each gated population, a progression tree was drawn, where each node Was color-coded by the percentage of gated cells in that node.

Comparing Multiple Datasets

According to further specific embodiments of the invention compares multiple datasets (e.g., from multiple experiments or with different but overlapping staining panels or multiple experimental conditions). In such embodiments, after downsampling the cells in each individual experiment, the invention pools the downsampled data into a meta-downsampled dataset. The meta-downsampled dataset can be viewed as a meta-cloud that represents where a cell or sample can possibly be in the high-dimensional space defined by the features that are invariant across the different data sets, e.g., the core surface markers in the human bone marrow data. The invention derives a tree that represents the shape of the meta-cloud. By color-coding or other using distinguishing indicia for the tree using the intensities of the invariant features, the invention can annotate the tree and sketch out the phenotypic landscape of the meta-cloud. For a feature (marker) that varies across data sets, the feature's behavior can be visualized by contrasting the features intensities across different datasets (e.g., different experimental conditions). Furthermore, cells or samples in one individual dataset may not populate the entire meta-cloud. The invention can color-code the MST nodes using the change of cell frequencies between difference datasets, which allows visualization and analysis as to whether any phenotypes emerge or disappear in response to experimental conditions.

Example 3: Human Bone Marrow

Scalability, Computational Merging of Overlapping Staining Panels, and Identification of Surrogate Features that Define Functionally Distinct Cell Types Next-generation mass cytometry technology currently provides simultaneous measurement of 31 or more markers per cell. Such a capacity allows enough surface markers to delineate nearly all cell types in the human hematopoiesis, as well as additional functional markers to study cellular response to perturbations. A specific implementation according to specific embodiments of the invention was tested on a mass cytometry dataset of human bone marrow [14]. Single cell data from 30 individual stimulatory conditions were obtained. In one experiment, an immunophenotype panel with 31 cell surface antibodies was used to analyze one unstimulated bone marrow sample. The remaining 29 experiments, composed of 5 unstimulated samples and 24 samples under different perturbations, were measured by a functional staining panel with 13 core surface markers (CD3, 4, 8, 11b, 19, 20, 33, 34, 38, 45, 45RA, 90, 123, from the previous panel) and 18 intracellular targets that reflect intracellular signaling states [14]. The scalability of the inventions analysis and output was thus demonstrated as the invention organized the data in a cellular hierarchy, identified surrogate markers that define a functionally distinct cell type, and mapped intracellular signal activation of functional markers across a landscape of hematopoietic development.

Figure 5:
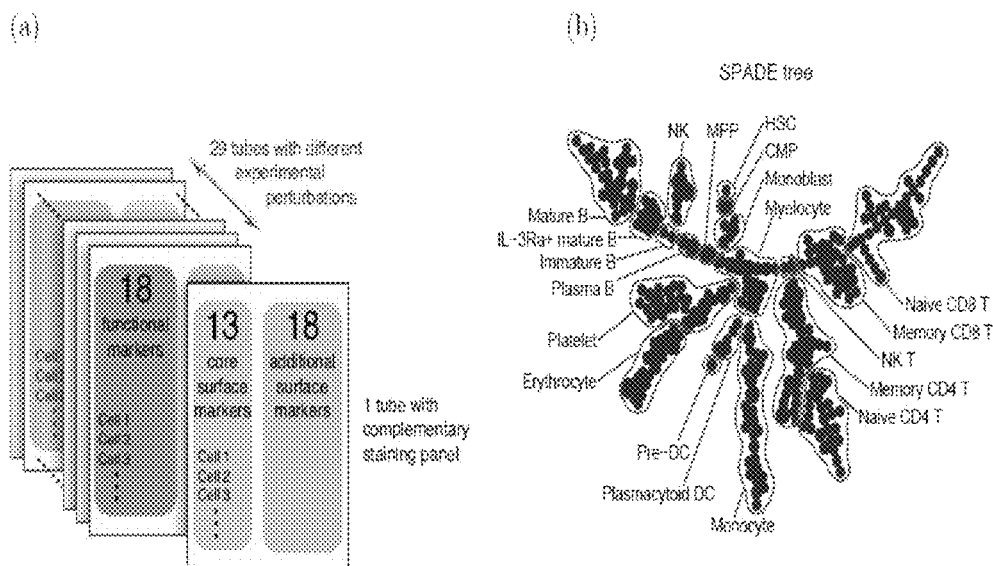
FIG. 5 illustrates outputs from the analysis according to the invention applied to a human bone marrow dataset of 30 experiments with two overlapping staining panels and multiple experimental conditions. (a) Experiment design. (b) SPADE tree, annotated according to the intensities of the 13 core surface markers.

The invention was applied to extract the underlying cellular hierarchy defined by the 13 core surface markers. Data from each experiment was downsampled separately. To integrate both staining panels, the downsampled cells of the six unstimulated samples were pooled as described herein. The pooled down-sampled cells were clustered into roughly 300 clusters. The number of clusters was larger than that of the previous mouse bone marrow analysis, because the increased number of markers could capture more cell types and branchpoints. Output of the resulting progression tree is shown in FIG. 5b and was annotated according to the variation of the 13 core surface markers (see FIG. 8 and FIG. 9). Many classically defined immune cell subsets were immediately visible in the progression tree according to the invention. Multiple nodes captured the heterogeneity of abundant cell types, including B cells (CD19+), T cells (CD3+), and dendritic cells (CD123+). By contrast, rarer cell types, such as hematopoietic stem cells (HSC) and multipotent progenitor cells (MPP) only occupied single nodes with high CD34 expression. The pattern of interconnectivity between these different cell types partially recapitulated established biology, as exemplified by the central positioning of the progenitor cell types, and the co-localization of multiple related T and B cell types.

Figure 6:
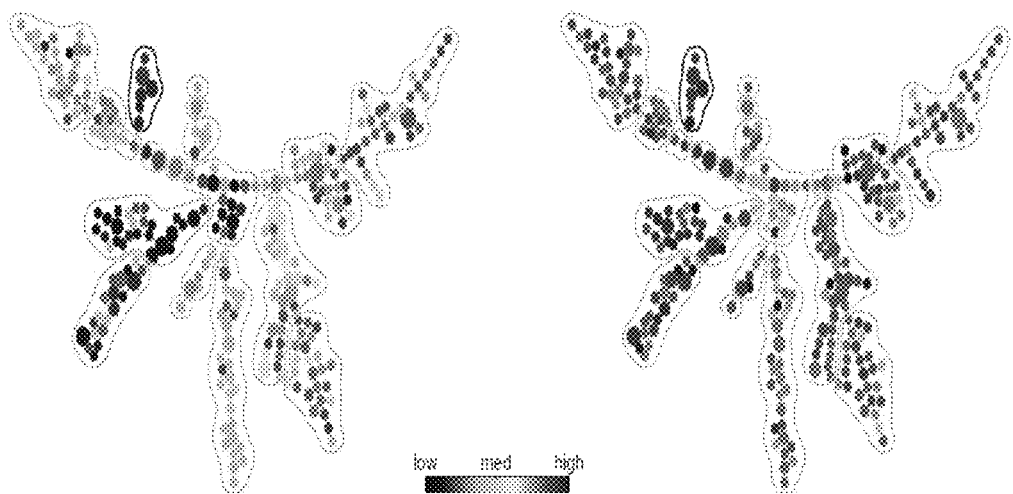
FIG. 6 illustrates outputs according to specific embodiments showing the tree color-coded by two NK specific markers CD7 and CD16.
Figure 8:
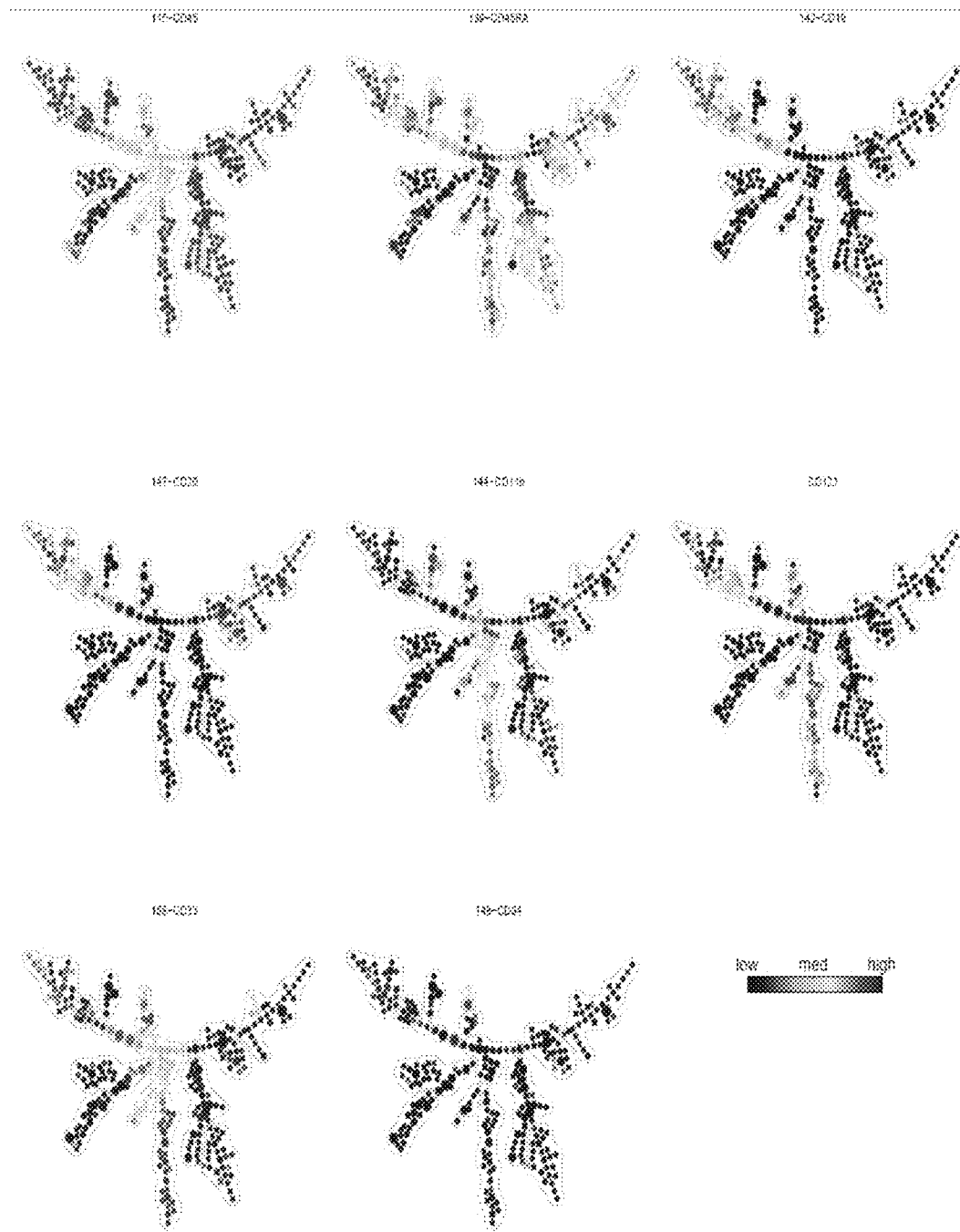
FIG. 8 illustrates outputs from the analysis according to the invention illustrating a progression tree derived from human bone marrow data, color-coded by CD45, CD45RA, CD19, CD20, CD11b, CD123, CD33 and CD34.
Figure 9:
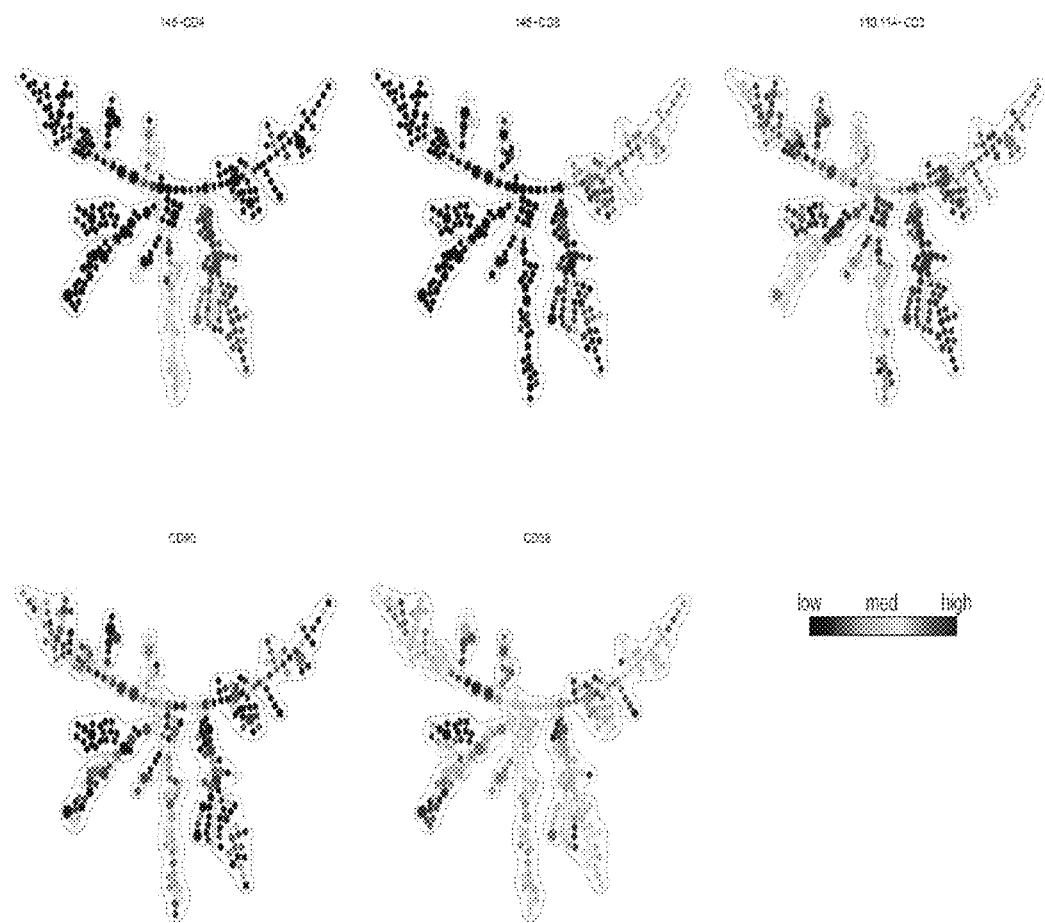
FIG. 9 illustrates outputs from the analysis according to the invention illustrating a progression tree derived from human bone marrow data, color-coded by CD4, CD8, CD3, CD90 and CD38.

These results demonstrate the utility of the invention for integrating complementary staining panels on a high-dimensional dataset. One particular group of nodes as illustrated in FIG. 6 (dark circle) exhibited a consistent CD38+ CD45RA+ phenotype (see FIG. 8 and FIG. 9), but the identity of this cell type was not clear based on any of the 13 core surface markers from which the progression tree was built. To annotate this cell type, we color-coded the tree with median intensities of the 18 non-core surface markers in the immunophenotype panel that were collected on one unstimulated bone marrow sample and not used by SPADE. As shown in FIG. 6, the unidentified nodes were found to be positive for CD7 and CD16, markers associated with NK cells. These results indicate that the invention reliably clustered a biologically relevant cell type, even in the absence of optimal markers considered standard in the immunology community as phenotypically representative for that cell type. FIG. 8 illustrates outputs from the analysis according to the invention illustrating a progression tree derived from human bone marrow data, color-coded by CD45, CD45RA, CD19, CD20, CD11b, CD123, CD33 and CD34. FIG. 9 illustrates outputs from the analysis according to the invention illustrating a progression tree derived from human bone marrow data, color-coded by CD4, CD8, CD3, CD90 and CD38. From these figures, the invention provides an output illustrating how surface markers behave across the tree. This output can be used to interpret the tree and generate new biological hypotheses.

Novel Dynamics of Intracellular Markers Revealed by Merging Datasets From Multiple Perturbation Conditions According to further specific embodiments, a tree derived by the invention (at times referred to as the SPADE Tree™) can be used to display the dynamics of intracellular markers or other features under different perturbations. For one intracellular marker and one perturbation, the invention can compute for each node (or cluster of cells) the ratio between the median intensities in the stimulated and unstimulated (basal) condition, and color-code all the nodes using this ratio.

Figure 7:
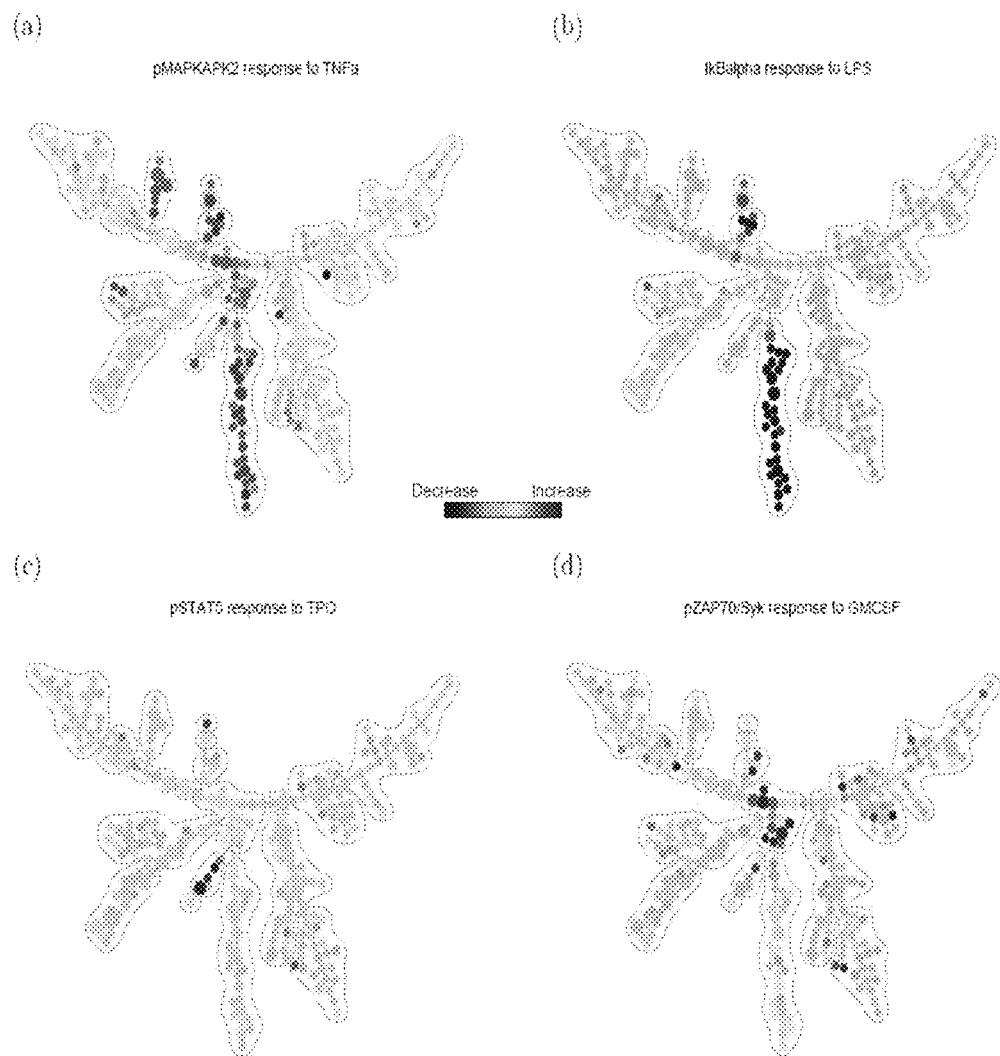
FIG. 7 illustrates outputs according to specific embodiments showing the tree color-coded by ratio of median intensity of intracellular markers between stimulated and unstimulated conditions.

In this example analysis, multiple well-established signaling functionalities were restricted to nodes with the expected cell phenotypes, which further verified the classifications and boundaries defined in FIG. 4, even though the analysis did not use the intracellular parameters to construct the progression tree. For example, TNF induction of phosphorylated MAPKAPK2 was observed in myeloid and NK cell types (FIG. 7). Similarly, the LPS-induced degradation of total IκB, an indicator of NFκB pathway activation, was restricted to cells of the monocytoid lineage, which uniquely express the receptor for LPS.

Such results can serve as a vehicle for data exploration and hypothesis generation, especially when color-coded by the intercellular signaling markers. For example, the induction of phosphorylated STAT5 after stimulation with thrombopoietin (TPO) was expected in HSCs and earlier myeloid progenitors [19]. While surprising, this observation may explain the enhanced production of plasmacytoid DCs observed in bone marrow treated with Flt3 ligand plus TPO, versus marrow treated with Flt3 ligand alone. Finally, the overlay of signaling dynamics facilitated the finding of GM-CSF-induced phosphorylation of pSyk in myelocytes. Similar signaling biology has been reported in neutrophils, which are the terminally differentiated progeny of myelocytes [18]. This analysis demonstrates how the invention according to specific embodiments can be used to map intracellular signal activation of functional markers across the landscape of human hematopoietic development.

Selecting Subpopulations of Cells or Samples ("Gating")

The construction and visualization of progression trees based on a set of features has several applications in: (a) gating, (b) discovering cellular hierarchy and (c) identifying uncharacterized markers by correlating their progression behavior to well-characterized markers.

The standard approach for gating flow cytometry data is to let users define regions either in one-parameter histogram graphical representations or two-parameter scatter plots. In such a case, users can only visualize the geometry and correlation of one or two markers in one plot. On the other hand, a progression tree according to specific embodiments of the invention represents the relationship among cell clusters in higher-dimensional spaces defined by the multiple markers or other characteristics associated with the data set. By referencing the progression tree to the traditional two-parameter scatter plots, users are able to determine which nodes (e.g., cell clusters) in the high-dimensional space correspond to undesired cell subpopulations to be excluded. Moreover, since each node in the progression tree corresponds to a cell cluster, gating can be easily performed by removing nodes from the progression tree. Thus, according to specific embodiments, the invention can be used for automatic gating of cell subpopulations or for enhancing a user's ability to manually gate cells in a large parameter data set.

Discovering Underlying Cellular Hierarchy

According to specific embodiments, the progression tree can be used to discover progression and differentiation hierarchy in flow data. This is illustrated with two examples below, one on simulated data and the other on B cell flow cytometry data. These are examples only and the invention has applications to many other data sets as discussed herein.

Example a: Discovering Underlying Cellular Hierarchy on Simulated Data

Figure 10:
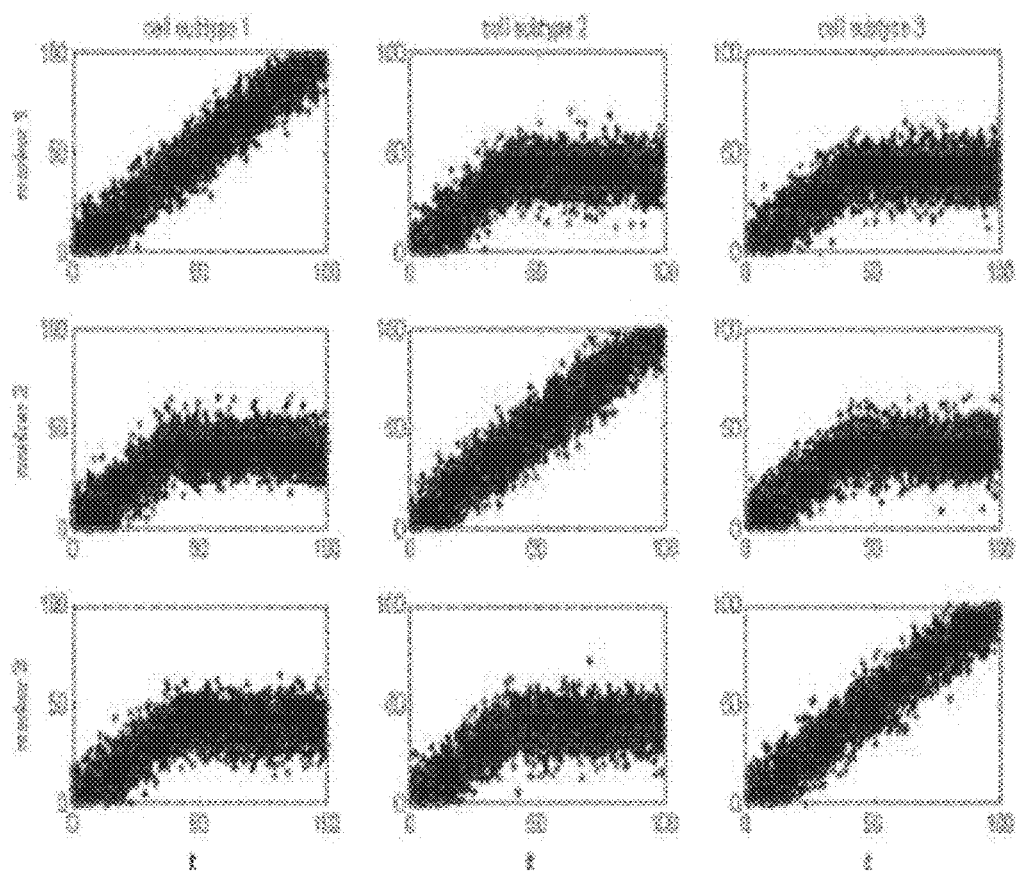
FIG. 10 illustrates an example of simulated data showing the progression of three markers in the three subpopulations of cells (where t is time) according to specific embodiments of the invention.

Consider a simulated population of cells that contains three subtypes with three simulated protein markers. FIG. 10 illustrates an example of simulated data showing the progression of three markers in the three subpopulations of cells (where t is time) according to specific embodiments of the invention. The figure shows the simulation ground truth of the progression of the three cell subtypes; in other words, each point in the figure represents a simulation of a cell that over time shows some difference in one or more protein markers. Time is indicated by the horizontal lines in each plot. For cells in subtype 1, marker 1's intensity increases during the progression, while markers 2 and 3 first increase and then saturate, which can be seen in the figure by examining the first column. For cell subtype 2, shown in the second column, marker 2 keeps increasing while markers 1 and 3 first increase and then saturate. In cell subtype 3, marker 3 keeps increasing. The width of the curves depends on the simulation noise. Therefore, in the three dimensional space spanned by the three markers, the progression of the entire population starts off at all three markers low, and then all three markers gradually increase (this is the common part of the three subtypes). Up to some point, the progression splits to three branches, each of which corresponds to one subtype.

Figure 11:
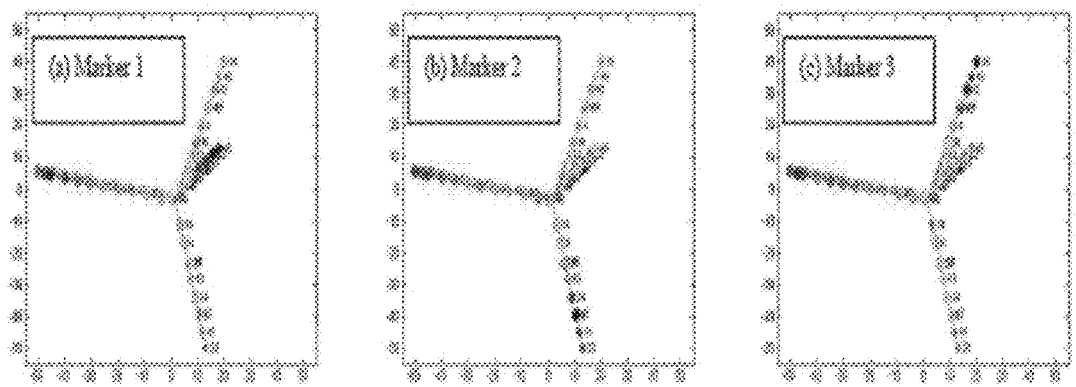
FIG. 11 illustrates an example of a progression tree constructed from the simulated data above, color-coded by (a) Marker 1, (b) Marker 2, and (c) Marker 3 showing the progression of three markers in the three subpopulations of cells (where t is time) according to specific embodiments of the invention.

FIG. 11 illustrates an example of a progression tree constructed from the simulated data above, color-coded by (a) Marker 1, (b) Marker 2, and (c) Marker 3 showing the progression of three markers in the three subpopulations of cells (where t is time) according to specific embodiments of the invention. This illustrates an example application of an embodiment of the invention to the simulated data set illustrated in FIG. 10. In this example, the topologies of the three plots are identical. The difference is that the nodes of each progression tree are color coded according to a different marker. Blue means low measured intensity; green and yellow represent medium intensity; and red means high intensity. FIG. 11 we see that starting from the left-most node, marker 1 has low intensity and gradually increases. Up to some point, the progression branches off. In one of the three branches, marker 1 continues to increase (cell subtype 1). In the other two branches, subtype 2 & 3, marker 1 stays at the same intensity level. Similar pattern can be observed for the other two markers. Therefore, the progression tree correctly captures the progression and differentiation hierarchy in the simulated data, where each branch after the split represents one of the three simulated cell subtypes.

Example b: Discovering Underlying Cellular Hierarchy on Real B-Cell Data

Figure 12:
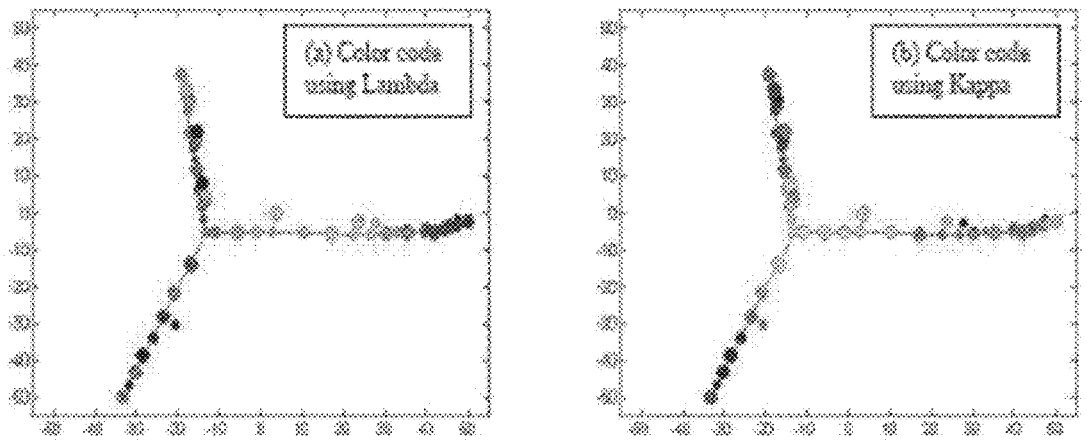
FIG. 12 illustrates an example of a progression of B cell development data based on markers (a) Lambda and (b) Kappa according to specific embodiments of the invention.

FIG. 12 illustrates an example of a progression of B cell development data based on markers (a) Lambda and (b) Kappa according to specific embodiments of the invention. This further demonstration example involved analyzing a flow cytometry dataset of B-cell development. It is known that markers Lambda and Kappa are mutually exclusive during B cell development, resulting in two subpopulations. In FIG. 12 the reconstructed progression tree, color coded by the intensities of Lambda and Kappa, respectively, indicates nodes in the bottom left branch that represent relatively early stages of B cell development, where Lambda and Kappa are both negative. After the split, the two braches represents the mutual exclusion of Kappa and Lambda. The upper branch represents the Kappa-positive Lambda-negative population. The other branch represents the Lambda-positive Kappa-negative population.

Characterizing Unknown Markers

Figure 13:
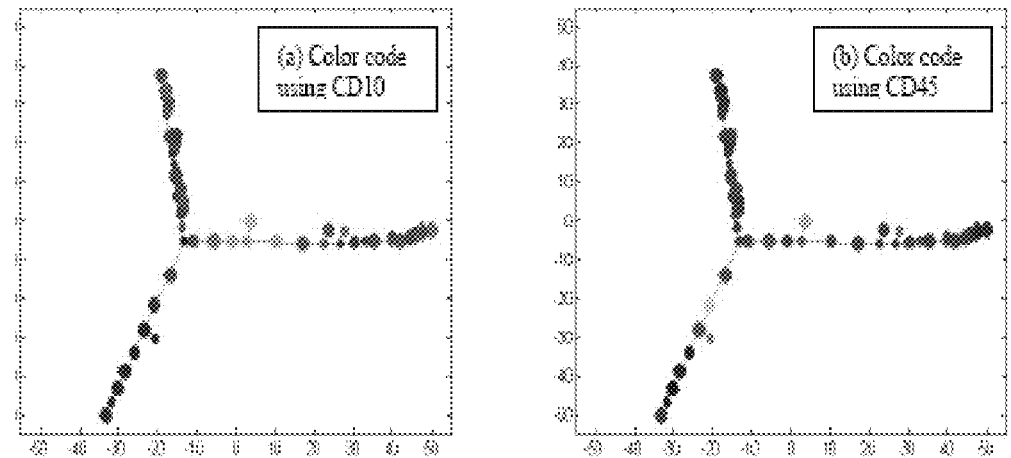
FIG. 13 illustrates an example of a progression of B cell development data based on markers (a) Lambda and (b) Kappa according to specific embodiments of the invention.

FIG. 13 illustrates an example of a progression of B cell development data based on markers (a) Lambda and (b) Kappa according to specific embodiments of the invention. Trees are color coded according to (a) CD10 and (b) CD20, respectively. The progression tree facilitates the identification of correlation between uncharacterized markers and the progression defined by sets of well-characterized markers. Continue with the B cell development example, after identifying the Lambda-Kappa split during B cell development, the invention can color code the nodes using other markers, to examine how other markers change with respect to the progression defined by Lambda and Kappa. FIG. 6 illustrates that CD10 is high before the Lambda-Kappa split and low after the split, while CD45 behaves oppositely. Therefore, markers CD10 and CD45 are correlated with the Lambda-Kappa split. Such information cannot be obtained using the traditional two-parameter scatter plot analysis.

Discovery of Features (e.g., Cellular Markers) that Drive Cellular Hierarchy

As discussed above, the cellular hierarchy determined according to specific embodiments of the invention can be used for gating, discovering differentiation hierarchy, and identify correlation between features, if a proper set of features (features) is chosen to construct the progression tree. However, the proper set of features is not always known a priori. Therefore, according to specific embodiments, the present invention further is able to computationally identify relevant features in terms of progression. In this embodiment, the invention clusters cells into clusters using all the measured features, regardless of whether they are relevant or not. One progression tree is constructed based on each feature, and the invention cross compares all the features and all the progression trees.

Denote $D_K$ as the distance matrix derived from feature K, where $D_{K(i,j)}$ is the Euclidean distance between feature K's average intensities in nodes (cell clusters) i and j. Denote $A_{L(i,j)}$ A L as the adjacency matrix of the progression tree constructed based on feature L, where $A_{L(i,j)}$ if nodes i and j are connected in the tree; otherwise $A_{L(i,j)}=0$.

The statistical fit between feature K and progression tree L is defined as follows, $$S_{K,L} = \sum_{A_{L(i,j)}=1} D_{K(i,j)} \qquad (1)$$

Permutation analysis is performed to assess the statistical significance of s. Permuted data are obtained by reshuffling the rows and corresponding columns of the distance matrix $D_K$. The p-value is the likelihood of obtaining a smaller s during random permutations. A p-value threshold is used to determine whether a feature and a progression tree fit well with each other. After statistically comparing all the features and all the progression trees, we derive a similarity matrix, whose (u, v) element is the number of trees that features u and v both fit well with. This similarity matrix describes the similarity between features in terms of progression.

Figure 14:
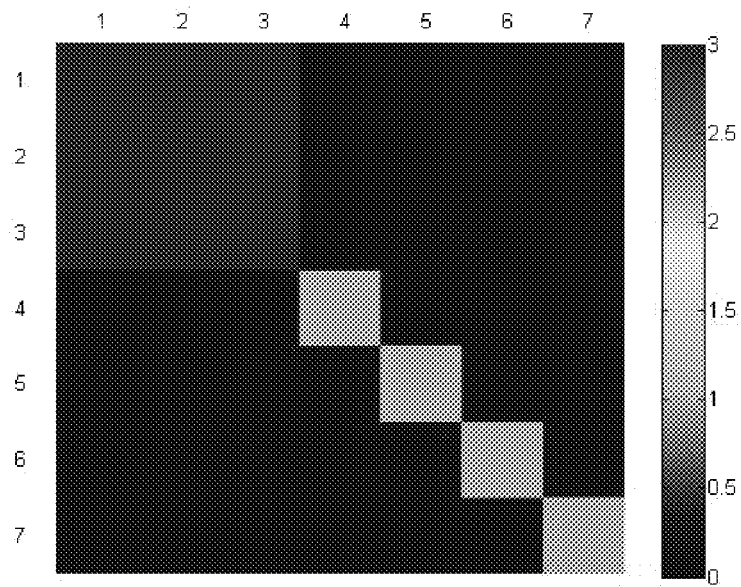
FIG. 14 illustrates an example plot showing a marker similarity matrix for identification of progression related markers according to specific embodiments of the invention.

When visualizing the feature similarity matrix, features are rearranged by hierarchical clustering of the columns of the similarity matrix to place similar features along the diagonal [4]. If there is a diagonal block whose entries all have relatively high values, the corresponding features are similar because they describe a common progression. The common progression and the supporting features are likely to be biologically meaningful. The statistical test in equation (1) is designed specifically for identifying similarity in terms of progression. Features that fit well with the same progression tree do not necessarily correlate with each other, meaning that this approach is able to identify similarities that correlation and regression types of analysis cannot. To illustrate the ability of the proposed method in identifying relevant features, we use the simulation example in the previous section. In addition to the three features that are relevant to the progression underlying the simulated cell population, we add another four features that are generated by random noise. The feature similarity matrix is shown in FIG. 14. The red block in the upper left corner indicate that features 1, 2 and 3 are similar to each other because they all fit well with a common set of three progression trees, while features 4, 5, 6 and 7 do not share similarity with any other features. This result shows that features 1, 2 and 3 are relevant to the progression underlying the simulated data, which is consistent with the simulation ground truth.

Other Embodiments

The clustering step in the present invention can be replaced by a variety of clustering algorithms, such as k-means, hierarchical clustering, mixture models, affinity prorogation, etc. The bottom line is that, a clustering algorithm is need to group together cells that are similar to each other.

The distance metric used in the MST construction and subsequent statistical comparison is the Euclidean distance. The Euclidean distance can be replace by other well defined distance metrics, such as L-1 distance, L-infinite distance, correlation, mutual information, etc. Different choices of the distance metric will lead to different identified progression tree among the sample. From our experience, the Euclidean distance works well for multiple datasets we have tested.

Embodiment in a Programmed Information Appliance

Figure 15:
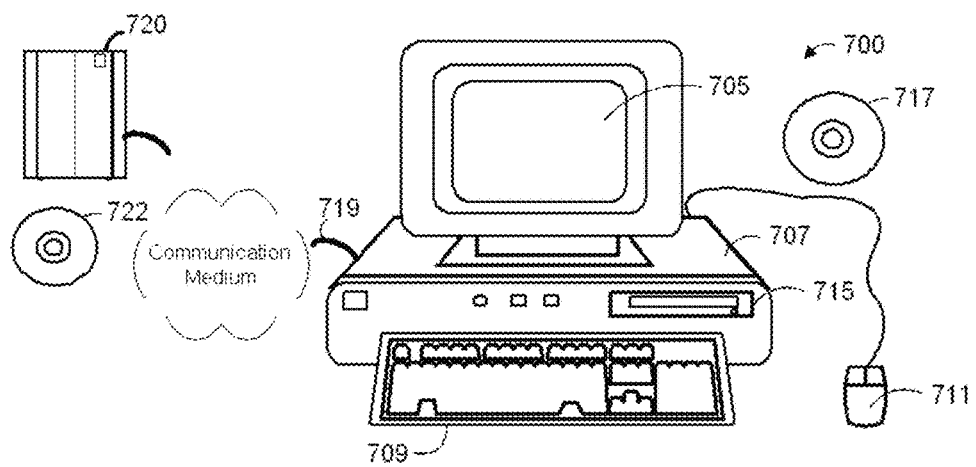
FIG. 15 is a block diagram showing a representative example logic device in which various aspects of the present invention may be embodied.

FIG. 15 is a block diagram showing a representative example logic device in which various aspects of the present invention may be embodied. As will be understood from the teachings provided herein, the invention can be implemented in hardware and/or software. In some embodiments, different aspects of the invention can be implemented in separate systems. For example, data collection, validation and storage may take place in one system. Data analysis may take place in a different system. Output and display may be performed by a third system. Moreover, the invention or components thereof may be embodied in a fixed media program component containing logic instructions and/or data that when loaded into an appropriately configured computing device cause that device to perform according to the invention. A fixed media containing logic instructions may be delivered to a user on a fixed media for physically loading into a viewer's computer or a fixed media containing logic instructions may reside on a remote server that a viewer accesses through a communication medium in order to download data or a program component.

FIG. 15 shows an information appliance or digital device 700 that may be understood as a logical apparatus that can perform method steps as described herein and provide visual or audio or printed output of the analysis as described and illustrated herein and/or transmit signals or data to other equipment as understood in the art and described herein. Such a device can be embodied as a general-purpose computer system or workstation running logical instructions to perform according to specific embodiments of the present invention. Such a device can also be custom and/or specialized laboratory or scientific hardware that integrates logic processing into a machine for performing various sample handling and data capture operations. In general, the logic processing components of a device according to specific embodiments of the present invention is able to read instructions from media 717 and/or network port 719, which can optionally be connected to server 720 having fixed media 722. Apparatus 700 can thereafter use those instructions to direct actions or perform analysis as understood in the art and described herein. One type of logical apparatus that may embody the invention is a computer system as illustrated in 700, containing CPU 707, optional input devices 709 and 711, storage media (such as disk drives) 715 and optional presentation or display device 705, which can represent any type of device for presenting visual output and can include speakers for presenting audio output, as will be understood in the art. Fixed media 717, or fixed media 722 over port 719, may be used to program such a system and may represent a disk-type optical or magnetic media, magnetic tape, solid state dynamic or static memory, etc. The invention may also be embodied in whole or in part as software recorded on a fixed tangible media, such as a disk drive, ROM, or other storage device. Communication port 719 may also be used to initially receive instructions that are used to program such a system and may represent any type of communication connection.

Figure 16:
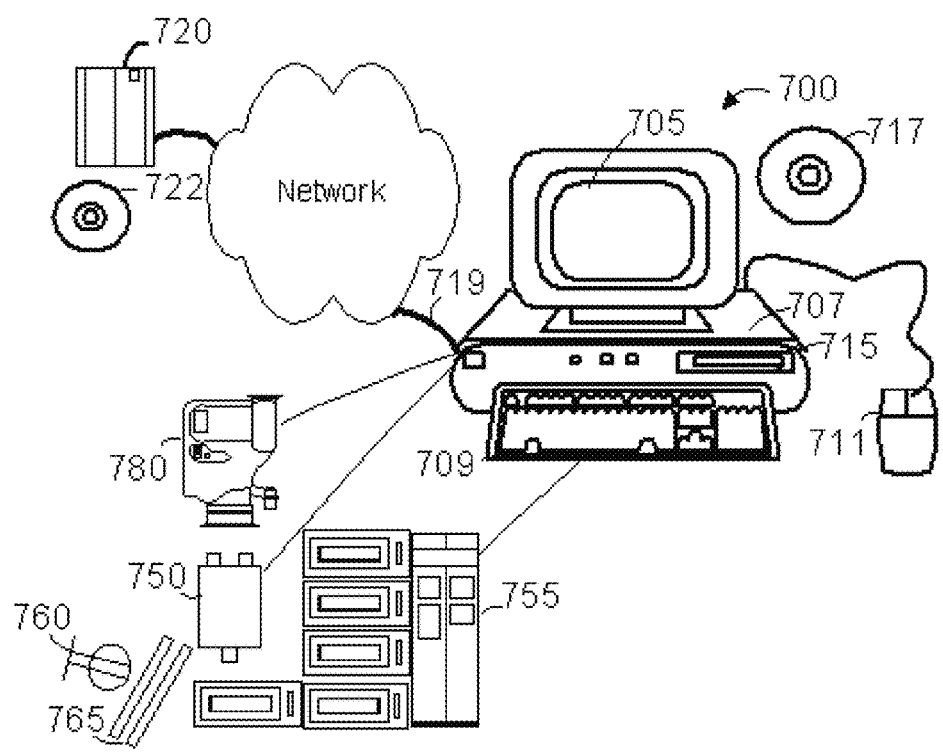
FIG. 16 is a block diagram illustrating various embodiments of the present invention incorporated into a microarray processing and analysis system further including wet or physical processing and/or delivery of a physical result and/or output of results data.

FIG. 16 shows additional components that can be part of a diagnostic system in some embodiments. These components include a microscope or viewer or detector 750, sampling handling 755, light source 760 and filters 765, and a CCD camera or capture device 780 for capturing digital images that may represent feature expression levels from a microarray via luminance detection, such as from microarray 785. It will be understood to those of skill in the art that these additional components can be components of a single system that includes logic analysis and/or control. These devices also may be essentially stand-alone devices that are in digital communication with an information appliance such as 700 via a network, bus, wireless communication, etc., as will be understood in the art. It will be understood that components of such a system can have any convenient physical configuration and/or appearance and can all be combined into a single integrated system. Thus, the individual components shown in FIG. 16 represent just one example system.

The invention also may be embodied in whole or in part within the circuitry of an application specific integrated circuit (ASIC) or a programmable logic device (PLD). In such a case, the invention may be embodied in a computer understandable descriptor language recorded on a tangible digital media, which may be used to create an ASIC, or PLD that in a logic system performs method steps as herein described.

Other Embodiments

The invention has now been described with reference to specific embodiments. Other embodiments will be apparent to those of skill in the art. In particular, a digital information appliance has generally been illustrated as a personal computer or laboratory workstation. However, the digital computing device is meant to be any information appliance suitable for performing the logic methods of the invention, and could include such devices as a digitally enabled laboratory systems or equipment, digitally enabled televisions, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims. All publications, patents, and patent applications cited herein or filed with this application, including any references filed as part of an Information Disclosure Statement, are incorporated by reference in their entirety.

Although only a few embodiments have been disclosed in detail above, other embodiments are possible and the inventor intends these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art. For example, while microarrays are described in the embodiments, other embodiments may use other kinds of readout. Moreover, as described herein, the output trees are visualization tools, and the computer techniques described herein need not actually make any kind of scatter plot.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be an Intel (e.g., Pentium or Core 2 duo) or AMD based computer, running Windows XP or Linux, or may be a Macintosh computer. The computer may also be a handheld computer, such as a PDA, cellphone, or laptop.

The programs may be written in C or Python, or Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attached Storage (NAS), or other removable medium, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned or can be understood from the teachings herein to those of skill in the art. Where a specified logical sense is used, the opposite logical sense is also intended to be encompassed.

What is claimed:

1. A computer implemented method for clustering and visualization of multicolor flow cytometry data, the method comprising:
   receiving cell samples from at least one subject;
   analyzing the cell samples using a flow cytometer, thereby yielding a multi-dimensional data set comprising cell sample points, wherein each cell sample point provides information about a measurement of a feature of a single cell sample;
   estimating a density function for the cell sample points in the multi-dimensional data set using a computing device;
   creating a down-sampled data set by removing a portion of the cell sample points in dense regions of the multi-dimensional data set using the computing device, wherein the dense regions are determined by the density function, wherein said creating comprises:
      determining a local density for each cell sample in said multi-dimensional data set using said computing device;
      downsampling cell sample points with local densities above a target density, so that their local densities reduce to approximately the target density after downsampling; and
      preventing downsampling of cell sample points with local densities less than said target density;
   clustering the cell sample points in the down-sampled data set into a plurality of sample clusters using the computing device;
   creating at least one progression tree in a Euclidean space using the computing device, wherein the at least one progression tree represents a progression among the plurality of sample clusters and reveals features associated with the progression;
   rendering an image using the created at least one progression tree using the computing device, wherein the image graphically shows a progressive relationship underlying the plurality of sample clusters using the computing device;
   receiving user inputs for the rendered image to interactively select a set of progressively related portions of the plurality of sample clusters;
   gating the multi-dimensional data set based on the selected sets of portions; and
   interactively rendering and displaying the gated multi-dimensional data set in response to received user inputs using the computing device.

2. The method of claim 1 further wherein:
   the multi-dimensional data set comprises an array of M samples by N features;
   the down-sampled data set comprises a down-sampled array of M* samples by N* features;
   the plurality of sample clusters comprise C clusters.

3. The method of claim 1, wherein rendering the image comprises:
   creating a visual representation of the at least one progression tree, wherein the visual representation shows data indicating intensity of at least one of the features.

4. The method of claim 1 further comprising:
   storing additional numerical feature values in the multi-dimensional data set, the additional numerical feature values not used in creating the down-sampled data set or clustering the cell sample points;
   wherein rendering the image comprises creating a representation of the at least one progression tree, the representation comprising a plurality of nodes and a plurality of edges connecting the plurality of nodes, wherein each of the plurality of edge includes a distance values, wherein a portion of the representation is in a color that is different from the remaining portion of the representation, the distance values and connection of nodes indicating a progression of the cell samples points using said features, and color or other indicators of said nodes or said tree indicating at least one additional numerical feature value.

5. The method of claim 1 further comprising:
   selecting a first subset of said features to use for said creating the down-sampled data set;
   selecting a second subset of said features to use for said clustering; and
   selecting a third subset of said features to use for said creating the at least one progression tree.

6. The method of claim 1 further wherein said cell samples comprise a plurality of cells and said features comprise a number of detectable cellular features or characteristics, the method further providing:
   constructing and outputting progression trees based on a selected subset of features to perform gating.

7. The method of claim 1 further wherein:
   abundant and rare cell sample types are relatively equally represented, and rare sample types are more likely to form their own clusters; and the number of cell sample points in said multi-dimensional data set is significantly reduced while most cell sample points of the rare sample type remain after downsampling and an overall distribution or shape of cell samples in the array of the original dataset is preserved.

8. The method of claim 1 further comprising:
after said clustering is complete, said computing device upsamples the cluster data by assigning each cell sample in the original dataset to a cluster and said upsampling comprises:
calculating median intensity and other statistics of each cluster with high accuracy; assigning each cell sample in the original dataset to one cluster by determining its nearest neighbor in the down-sampled data set and assigning the sample to the cluster that the nearest neighbor in the downsampled data belongs to.

9. The method of claim 1 further wherein creating the progression tree comprises:
defining a fully connected undirected weighted graph comprising a plurality of nodes and a plurality of edges connecting the nodes, wherein each node represents one sample cluster;
determining a weight on the edge that connects nodes i and j is defined as the Euclidean distance between the feature expressions of sample clusters i and j;
applying Boruvka's algorithm to derive the MST from the fully connected graph, such that starting from one cluster and moving along the edges of the MST, a gradual change of feature expression levels is observed.

10. The method of claim 1 further comprising:
analyzing dynamics of features under different perturbations;
such that for a feature and a perturbation, determining for each cluster a ratio between the median intensities of features in an unstimulated condition and the median intensities of features in a stimulated condition;
indicating dynamics of features under perturbations in said outputting of cluster representations in said trees using said ratio.

11. The method of claim 1 further comprising:
determining from said progression tree, one or more progression branches; comparing said progression branches across multiple features; and associating said branches with one or more progression states of said samples.

12. The method of claim 1 further wherein said samples comprise a plurality of cells and said features comprise a number of detectable cellular features or characteristics, the method further providing identifying uncharacterized features by correlating their progression behavior to well-characterized features.

13. The method of claim 1 further comprising:
determining a progression similarity matrix between two or more features indicating a number of progressions supported in common by the feature;
wherein the progression similarity matrix is an integer count of progression trees concordant with the feature according to a selected threshold.

14. The method of claim 13 further wherein the progression similarity matrix quantifies the progression similarity between pairs of features, wherein the u; v element of the progression similarity matrix is a number of progression trees that are concordant with both features u and v.

15. The method of claim 1 further comprising:
receiving into a provided memory readable and writable by a provide CPU flow cytometry data, said flow cytometry data containing data values indicative of plurality of features measured for a larger plurality of samples;
clustering samples into a smaller number of sample clusters, where clusters are determined by comparing features across multiple samples from the received flow cytometry data;
determining per-feature progressions for one or more selected features from the flow cytometry data;
identifying progression-similar features by identifying which features have high progression similarity to multiple per-feature progressions;
using the progression-concordant features to determine a most likely overall progression of samples from flow cytometry data; and
outputting said most likely overall progression of flow cytometry samples to a user using a provided computer output device.

* * * * *